United States Patent
Madjarov et al.

(10) Patent No.: US 9,883,908 B2
(45) Date of Patent: Feb. 6, 2018

(54) DEVICES, SYSTEMS, AND METHODS FOR TREATING CARDIAC ARRHYTHMIAS

(71) Applicant: The Charlotte-Mecklenburg Hospital Authority, Charlotte, NC (US)

(72) Inventors: Jeko Metodiev Madjarov, Charlotte, NC (US); John Michael Fedor, Charlotte, NC (US); Jackie H. Kasell, Matthews, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 1114 days.

(21) Appl. No.: 13/875,502

(22) Filed: May 2, 2013

(65) Prior Publication Data
US 2013/0296852 A1 Nov. 7, 2013

Related U.S. Application Data

(60) Provisional application No. 61/641,569, filed on May 2, 2012, provisional application No. 61/752,719, filed on Jan. 15, 2013.

(51) Int. Cl.
*A61B 5/042* (2006.01)
*A61B 18/14* (2006.01)
(Continued)

(52) U.S. Cl.
CPC .......... *A61B 18/1492* (2013.01); *A61B 5/042* (2013.01); *A61B 5/04082* (2013.01);
(Continued)

(58) Field of Classification Search
CPC ... A61B 5/6834; A61B 18/14; A61B 18/1492; A61B 2018/142; A61B 2018/1425; A61B 2018/1475; A61B 2018/00291
(Continued)

(56) References Cited

U.S. PATENT DOCUMENTS 4,685,466 A * 8/1987 Rau ................... A61B 5/04082
600/387
5,247,945 A 9/1993 Heinze et al.
(Continued)

FOREIGN PATENT DOCUMENTS

WO  WO-99/42046 A1  8/1999
WO  WO-02/094115 A2  11/2002

OTHER PUBLICATIONS

International Search Report and Written Opinion for Application No. PCT/US2013/039279, dated Oct. 7, 2013.
(Continued)

*Primary Examiner* — Lee S Cohen
*Assistant Examiner* — Erin M Cardinal
(74) *Attorney, Agent, or Firm* — John P. Zimmer; Smith Moore Leatherwood LLP

(57) ABSTRACT

Medical devices are described for performing mapping, ablating, and/or pacing procedures on one or more layers of the cardiac wall via an epicardial approach in a minimally invasive (e.g., orthoscopic) surgical procedure. One of the medical devices described includes a main support member and one or more secondary support members extending outwardly from the main support member having electrodes configured to receive electrical impulses. The secondary support member may include a support pad configured to be removably attached to a corresponding area of the epicardium for holding the medical device in place during a procedure, such as through application of vacuum pressure via a containment dome provided on each secondary support member. Further, an ablating electrode may be slidably disposed along the main support member for transmitting energy to a target site proximate the electrode. Associated methods are also described.

23 Claims, 20 Drawing Sheets

(51) Int. Cl.

| | |
|---|---|
| *A61B 18/12* | (2006.01) |
| *A61B 5/0408* | (2006.01) |
| *A61N 1/05* | (2006.01) |
| *A61N 1/36* | (2006.01) |
| *A61N 1/06* | (2006.01) |
| *A61B 18/00* | (2006.01) |

(52) U.S. Cl.
CPC .......... *A61B 18/148* (2013.01); *A61N 1/0592* (2013.01); *A61N 1/36017* (2013.01); *A61B 2018/0016* (2013.01); *A61B 2018/00196* (2013.01); *A61B 2018/00267* (2013.01); *A61B 2018/00279* (2013.01); *A61B 2018/00291* (2013.01); *A61B 2018/00351* (2013.01); *A61B 2018/00577* (2013.01); *A61B 2018/00839* (2013.01); *A61B 2018/00982* (2013.01); *A61B 2018/143* (2013.01); *A61B 2018/1427* (2013.01); *A61B 2018/1435* (2013.01); *A61B 2018/1467* (2013.01); *A61B 2018/1475* (2013.01); *A61N 1/06* (2013.01)

(58) Field of Classification Search
USPC .................................. 606/41; 600/374, 387
See application file for complete search history.

(56) References Cited

U.S. PATENT DOCUMENTS

| | | | |
|---|---|---|---|
| 5,300,110 A | 4/1994 | Latterell et al. | |
| 5,471,982 A * | 12/1995 | Edwards | A61B 5/0422 600/374 |
| 5,476,495 A * | 12/1995 | Kordis | A61B 5/0422 600/374 |
| 5,549,661 A * | 8/1996 | Kordis | A61B 18/1492 600/374 |
| 5,885,278 A * | 3/1999 | Fleischman | A61B 18/1492 600/374 |
| 5,978,714 A | 11/1999 | Zadini et al. | |
| 6,014,579 A * | 1/2000 | Pomeranz | A61B 5/0422 600/374 |
| 6,029,091 A * | 2/2000 | de la Rama | A61B 18/1492 600/374 |
| 6,152,955 A | 11/2000 | KenKnight et al. | |
| 6,514,250 B1 * | 2/2003 | Jahns | A61B 18/1492 600/387 |
| 6,702,732 B1 | 3/2004 | Lau et al. | |
| 7,146,226 B2 | 12/2006 | Lau et al. | |
| 7,149,588 B2 | 12/2006 | Lau et al. | |
| 7,155,295 B2 | 12/2006 | Lau et al. | |
| 7,158,839 B2 | 1/2007 | Lau | |
| 7,164,952 B2 | 1/2007 | Lau et al. | |
| 7,181,272 B2 | 2/2007 | Struble et al. | |
| 7,187,984 B2 | 3/2007 | Lau et al. | |
| 7,225,036 B2 | 5/2007 | Lau et al. | |
| 7,587,247 B2 | 9/2009 | Schaer et al. | |
| 7,610,104 B2 | 10/2009 | Kaplan et al. | |
| 7,976,456 B2 | 7/2011 | Lau et al. | |
| 2002/0143326 A1 * | 10/2002 | Foley | A61B 18/1492 606/41 |
| 2003/0120268 A1 * | 6/2003 | Bertolero | A61B 1/12 606/32 |
| 2003/0236455 A1 | 12/2003 | Swanson et al. | |
| 2005/0137673 A1 | 6/2005 | Lau et al. | |
| 2005/0171589 A1 | 8/2005 | Lau et al. | |
| 2005/0273129 A1 * | 12/2005 | Michels | A61B 17/3415 606/185 |
| 2005/0288715 A1 | 12/2005 | Lau et al. | |
| 2006/0009831 A1 | 1/2006 | Lau et al. | |
| 2006/0025762 A1 * | 2/2006 | Mohan | A61B 18/1482 606/41 |
| 2006/0084960 A1 * | 4/2006 | Mester | A61B 5/117 606/15 |
| 2007/0043416 A1 | 2/2007 | Callas et al. | |
| 2007/0106359 A1 | 5/2007 | Schaer et al. | |
| 2008/0243119 A1 * | 10/2008 | Whayne | A61B 18/1492 606/49 |
| 2009/0143638 A1 * | 6/2009 | Keogh | A61B 17/0206 600/37 |
| 2009/0156892 A1 | 6/2009 | Lau et al. | |
| 2009/0299447 A1 | 12/2009 | Jensen et al. | |
| 2010/0312296 A1 | 12/2010 | Gray | |
| 2012/0271141 A1 * | 10/2012 | Davies | A61B 5/053 600/382 |

OTHER PUBLICATIONS

Partial International Search Report for Application No. PCT/US2013/039279; dated Aug. 2, 2013.

Cesario, D. A. et al., *Value of High-Density Endocardial and Epicardial Mapping for Catheter Ablation of Hemodynamically Unstable Ventricular Tachycardia*, Heart Rhythm, vol. 3, No. 1 (Jan. 2006), pp. 1-10.

Heist, E. K. et al., *Direct Visualization of Epicardial Structures and Ablation Utilizing a Visually Guided Laser Balloon Catheter: Preliminary Findings*, Journal of Cardiovascular Electrophysiology, vol. 22, No. 7 (Jul. 2011) pp. 808-812.

Horowitz, B. N. et al., *Percutaneous Intrapericardial Echocardiography During Catheter Ablation: A Feasiblity Study*, Heart Rhythm, vol. 3, No. 11 (Nov. 2006). pp. 1275-1282.

Ling, L-H. et al., *Multielectrode Catheter Ablation: Linear Ablation made Easy?*, J. Cardiovasc Electrophysiol., vol. 22 (2011) pp. 746-747.

Michowitz, Y. et al., *Hybrid Procedures for Epicardial Catheter Ablation of Ventricular Tachycardia: Value of Surgical Access*, Heart Rhythm, vol. 7, No. 11 (Nov. 2010) pp. 1635-1643.

Michowitz, Y. et al., *Electrophysiological Differences Between the Epicardium and the Endocardium of the Left Atrium*, PACE—Pacing and Clinical Electrophysiology, 34 (1) (2011) pp. 37-46.

Miyazaki, S. et al., *Initial Results of Efficacy of Left Linear Ablation Using a Novel Simultaneous Multielectrode Ablation Catheter*, Journal of Cardiovascular Electrophysiology, vol. 22, No. 7 (Jul. 2011) pp. 739-745.

Nakahara, S. et al., *Characterization of the Arrhythmogenic Substrate in Ischemic and Nonischemic Cardiomyopathy. Implications for Catheter Ablation of Hemodynamically Unstable Ventricular Tachycardia*, Journal of the American College of Cardiology, 55 (21) (2010) pp. 2355-2365.

Nakahara, S. et al., *Distribution of Late Potentials Within Infarct Scars Assessed by Ultra High-Density Mapping*, Heart Rhythm, 7 (12) (2010) pp. 1817-1824.

Shivkumar, K., *Percutaneous Epicardial Ablation of Atrial Fibrillation*, Heart Rhythm, vol. 5, No. 1 (Jan. 2008) pp. 152-154.

Tung, R. et al., *Accuracy of Combined Endocardial and Epicardial Electroanatomic Mapping of a Reperfused Porcine Infarct Model: A Comparison of Electrofield and Magnetic Systems With Histopathologic Correlation*, Heart Rhythm, vol. 8, No. 3 (Mar. 2011), pp. 339-447.

Tung, R. et al., *Distinguishing Epicardial Fat From Scar: Analysis of Electrograms Using High-Density Electroanatomic Mapping in a Novel Porcine Infarct Model*, Heart Rhythm, 7 (3) (2010) pp. 389-395.

Valderrabano, M. et al., *Percutaneous Epicardial Mapping During Ablation of Difficult Accessory Pathways as an Alternative to Cardiac Surgery*, Heart Rhythm, vol. 1, No. 3 (Sep. 2004), pp. 311-316.

\* cited by examiner

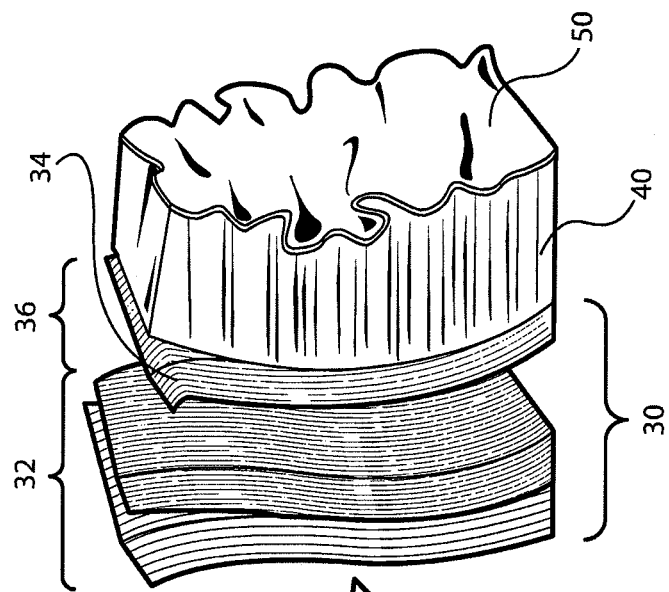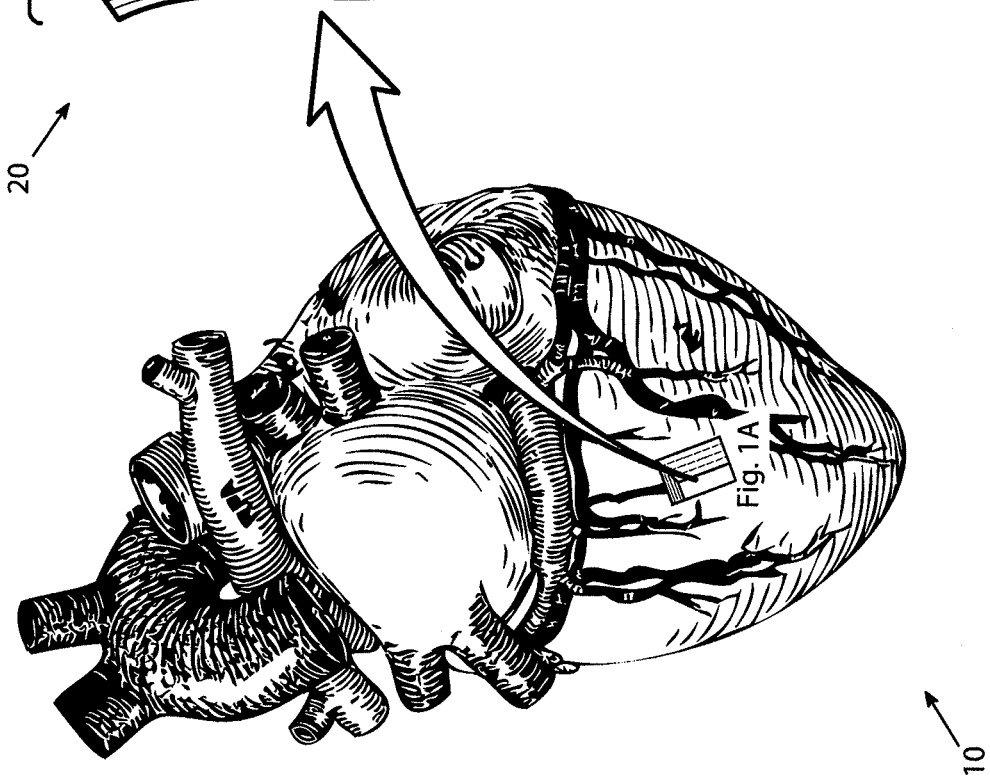

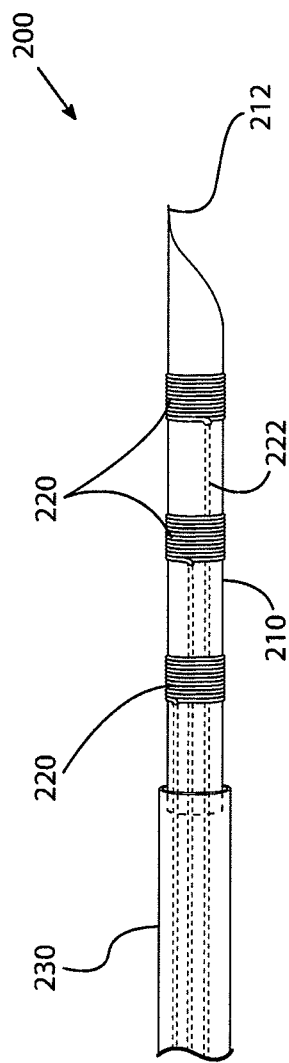
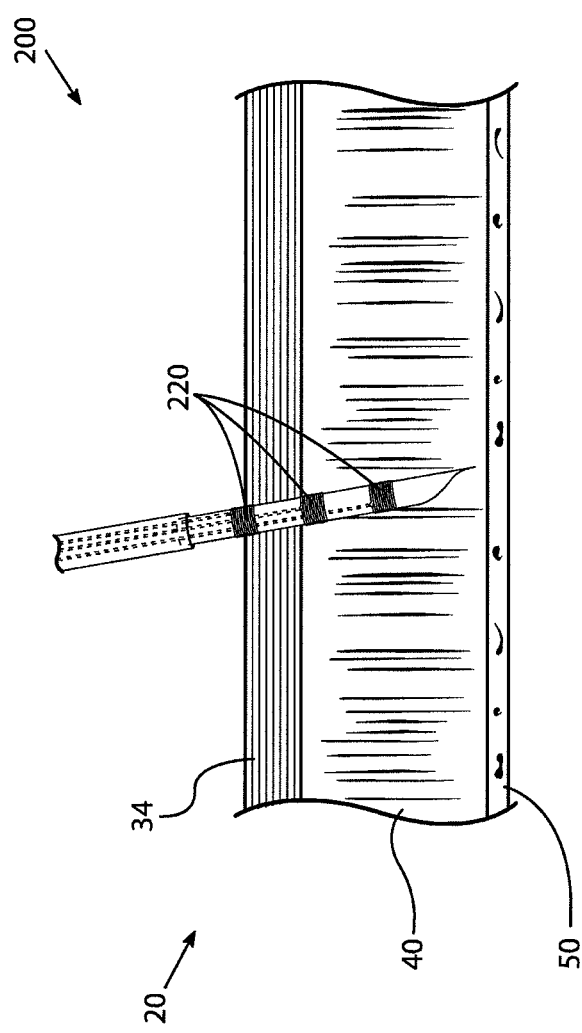
FIG. 7
FIG. 8

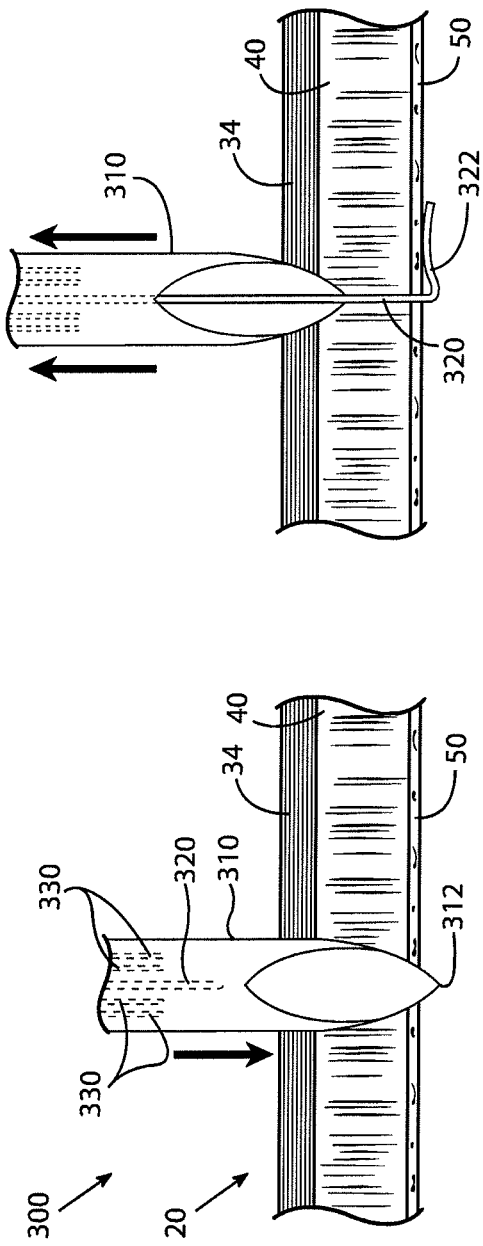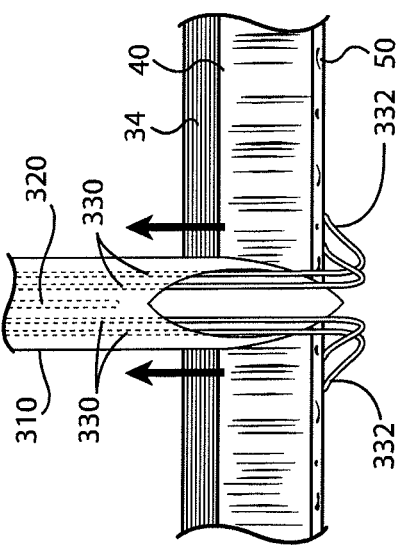

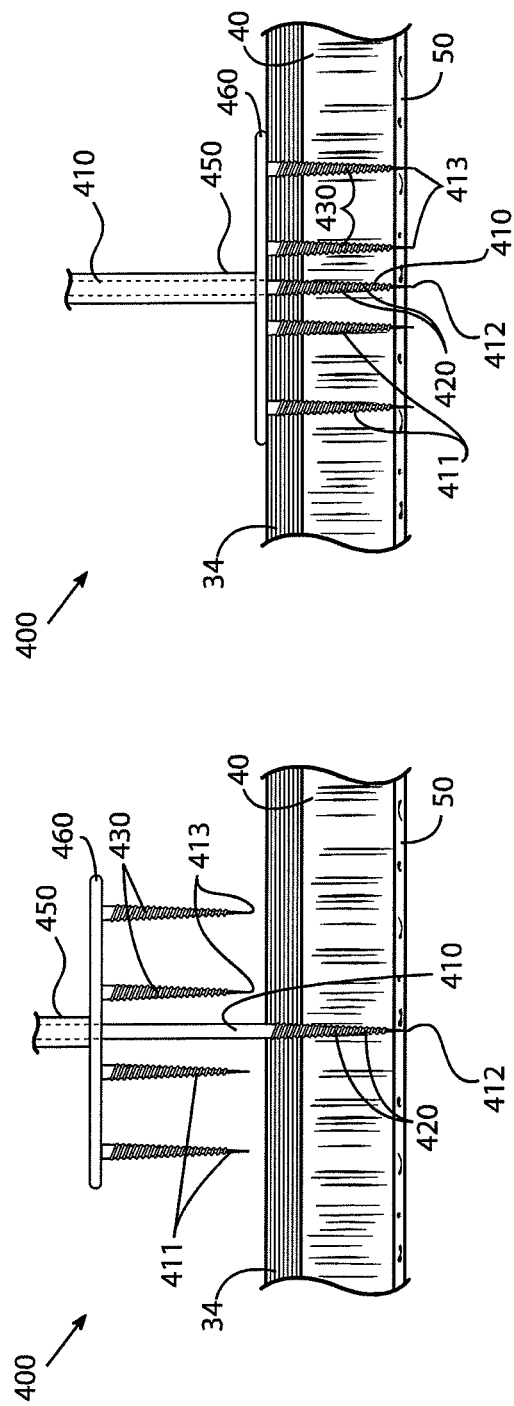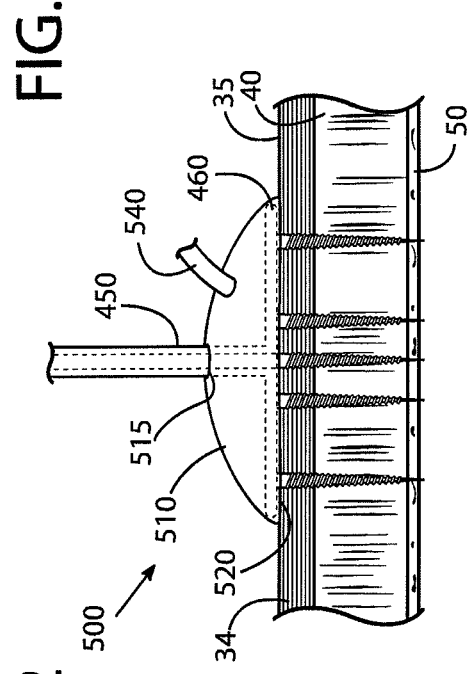

DEVICES, SYSTEMS, AND METHODS FOR TREATING CARDIAC ARRHYTHMIAS

CROSS-REFERENCE TO RELATED APPLICATIONS

This application claims the benefit of U.S. Provisional Application No. 61/641,569 entitled "Devices, Systems, and Methods for Treating Cardiac Arrhythmias," filed May 2, 2012, and U.S. Provisional Application No. 61/752,719 entitled "Devices, Systems, and Methods for Treating Cardiac Arrhythmias," filed Jan. 15, 2013, the contents of both of which are incorporated herein in their entirety.

FIELD OF THE INVENTION

The present invention relates generally to medical devices, systems, and methods for treating cardiac arrhythmias using minimally invasive surgical techniques. More specifically, methods and apparatuses are described for epicardially approaching a target site in a patient's heart and performing mapping, ablation, and/or pacing procedures.

BACKGROUND

The heart is one of the most important organs of the body. Electrical impulses normally generated at the sinoatrial node within the wall of the right atrium of the heart are typically carried by the heart's conducting tissue to different areas of the heart muscle, causing the left and right atria of the heart to contract first, followed by contraction of the left and right ventricles (a heartbeat). This controlled stimulation of the heart muscles provides for efficient contraction of all four chambers of the heart and allows blood to be pumped through the lungs and circulatory system.

Cardiac arrhythmias occur when the electrical impulses in your heart misfire, causing your heart to beat too quickly, too slowly, or irregularly. Cardiac arrhythmias may be caused by stress, medications, or a fever or other illness, and the occasional heart flutter or racing heart is often harmless. Other times, however, arrhythmias are caused by more serious conditions, such as damaged heart tissue (e.g., resulting from a heart attack), coronary artery disease, high blood pressure, diabetes, and hyperthyroidism, among other conditions, and in these cases the arrhythmias can be dangerous and potentially life-threatening.

Cardiac arrhythmias are generally classified as atrial or ventricular, based on where they originate, and as a tachycardia (a fast heartbeat) or a bradycarcia (a slow heartbeat), based on the number of beats per minute at rest. Although more rare than atrial arrhythmias, ventricular arrhythmias are typically considered more serious and can lead to a heart attack or sudden death.

In cases where the arrhythmia is caused by an abnormality in the cardiac tissue, the abnormality may be in any layer or in multiple layers of the heart. Accordingly, there is a need for devices, systems, and methods for treating arrhythmias in all layers of the heart in a manner that is safe, reproducible, simple to administer, effective, minimally invasive, and allows for faster recovery of the patient.

BRIEF SUMMARY OF EXAMPLE EMBODIMENTS

Accordingly, embodiments of systems, methods, and medical devices for treating cardiac arrhythmias using minimally invasive surgical techniques are provided. In one embodiment, a system treating cardiac arrhythmias is provided that includes a medical device comprising a plurality of mapping electrodes configured to receive electrical impulses and at least one ablating electrode configured to transmit energy to a target site proximate the ablating electrode. The system may also include an optical device configured to capture and transmit an epicardial view of the target site for facilitating positioning of the medical device at the target site. The medical device is configured to be delivered to the target site epicardially. In some cases, at least one of the mapping electrodes of the medical device may also serve as the ablating electrode.

In other embodiments, a medical device for treating cardiac arrhythmias is provided that includes a plurality of support members, at least one mapping electrode disposed along each support member, an ablating electrode, and a tubular member. The support members may be configured to be moved between an expanded position and a collapsed position, and the at least one mapping electrode may be configured to receive electrical impulses. The ablating electrode may be slidably disposed on one of the support members, and the ablating electrode may be configured to transmit energy to a target site proximate the ablating electrode. The tubular member may define a lumen therethrough, and the tubular member may be configured to receive the support members within the lumen when the support members are in the collapsed position. In the expanded state, the support members may define a coverage area, and the mapping electrodes may be configured to receive electrical impulses from corresponding locations of the target site across the coverage area. Furthermore, in the expanded state, the ablating electrode may be configured to be moved linearly along the respective support member to ablate a portion of the target site within the coverage area.

In some cases, the medical device may further include a guide member attached to the ablating electrode. The guide member may be movable by a user independently of the support members for positioning the ablating electrode.

In still other embodiments, a medical device for treating cardiac arrhythmias may be provided that comprises a support member defining a distal tip configured to penetrate a thickness of a cardiac wall and a plurality of electrodes disposed along the support member. Each electrode is configured to receive electrical impulses from a corresponding region within the cardiac wall during a mapping procedure and to transmit energy to the corresponding region within the cardiac wall during an ablation procedure. In some cases, each electrode may be configured to transmit energy independently of other electrodes during the ablation procedure. Additionally or alternatively, each electrode may be configured to transmit an electrical impulse for a predetermined period of time at a predetermined voltage during a pacing procedure.

In still other embodiments, a medical device for treating cardiac arrhythmias may be provided that includes a support member defining a distal tip configured to penetrate a thickness of a cardiac wall, at least one mapping electrode received within the support member, and a plurality of ablating electrodes. The at least one mapping electrode may be configured to receive electrical impulses from a corresponding region within the cardiac wall. In a retracted position of the mapping electrode, the mapping electrode may be disposed within a lumen of the support member and, in an extended position of the mapping electrode, an engagement end of the mapping electrode may be disposed outside the support member.

The ablating electrodes may be configured to transmit energy to a target site proximate a distal end of the ablating electrode. Each ablating electrode may be configured to be received within the lumen of the support member when the ablating electrodes are in a retracted position. Furthermore, each ablating electrode may define a distal hook portion when the ablating electrodes are in an extended position. In the extended position, the hook portion of each ablating electrode may be configured to extend away from the support member such that the distal hook portion of each ablating electrode engages a target site within the cardiac wall. The at least one of the mapping electrodes may, in some cases, also be configured to transmit energy to a target site proximate the mapping electrode.

In still other embodiments, a medical device for treating cardiac arrhythmias is provided comprising a first support member defining a distal tip configured to penetrate a thickness of a cardiac wall and a plurality of mapping electrodes disposed along the support member. Each electrode may be configured to receive electrical impulses from a corresponding region within the cardiac wall. The medical device may further include a tubular member defining a lumen therethrough, and the tubular member may be configured to receive the first support member within the lumen when the first support member is in a retracted position. In an extended position, the distal tip of the first support member may be disposed distally of a distal end of the tubular member and may penetrate the cardiac wall. The medical device may further include a transverse member, a plurality of second support members, and a plurality of ablating electrodes.

The transverse member may be disposed on the distal end of the tubular member and arranged substantially perpendicularly to the tubular member. Each of the plurality of second support members may define a distal tip configured to penetrate a thickness of the cardiac wall. Furthermore, each second support member may be fixed with respect to the transverse member and may be movable relative to the first support member via movement of the tubular member. In addition, at least one ablating electrode may be disposed along each second support member, and each ablating electrode may be configured to transmit energy to a target site proximate the ablating electrode.

In some cases, the tubular member may be integral with the transverse member. Additionally or alternatively, the transverse member may have a disk shape.

In still other embodiments, a method of treating cardiac arrhythmias is provided that includes making a first incision in a thoracic area of a patient's body; inserting a distal end of a medical device into the first incision; inserting an optical device into the second incision, where the optical device is configured to capture and transmit an epicardial view of the target site; positioning the distal end of the medical device proximate the target site using the epicardial view; and mapping the electrical impulses. The medical device may be configured to include a plurality of mapping electrodes configured to receive electrical impulses and at least one ablating electrode configured to transmit energy to a target site proximate the ablating electrode. The medical device may be configured to be delivered to the target site epicardially. Portions of cardiac tissue may be ablated using the medical device based on the electrical impulses received. In some embodiments, the method may further include pacing the patient's heart function using the medical device by transmitting an electrical impulse for a predetermined period of time at a predetermined voltage proximate the target site.

In still other embodiments, a medical device for treating cardiac arrhythmias is provided comprising at least two support members, a plurality of pacing electrodes disposed along each support member, and at least one attachment member disposed at an end of the support members and configured to secure the medical device to body tissue at the target site. The support members may be configured to be moved between an expanded position and a collapsed position, and each pacing electrode may be configured to transmit an electrical impulse for a predetermined period of time at a predetermined voltage proximate the target site. In the collapsed position, the medical device may be configured to be delivered to the target site epicardially, and the medical device may be configured to be moved from the collapsed position to the expanded position once the device is proximate the target site such that the attachment member secures the medical device in place for effecting artificial pacing of a patient's heart.

In some cases, the at least one attachment member may be coated with a material that is configured to dissolve after exposure to bodily fluids for a predetermined amount of time for allowing the at least one attachment member to secure the medical device in place. Additionally or alternatively, the plurality of pacing electrodes may be configured to selectively transmit the electrical impulse.

In still other embodiments, a medical device for treating cardiac arrhythmias is provided that includes a plurality of support members, wherein the support members are configured to be moved between an expanded position and a collapsed position. At least one mapping electrode configured to receive electrical impulses may be disposed on each support member, and an ablating electrode may be slidably disposed on one of the support members. The ablating electrode may be configured to transmit energy to a target site proximate the ablating electrode. In the expanded state, the support members may define a coverage area and the mapping electrodes may be configured to receive electrical impulses from corresponding locations of the target site across the coverage area. Furthermore, in the expanded state, the ablating electrode may be configured to be moved linearly along the respective support member to ablate a portion of the target site within the coverage area.

In some cases, the medical device may include a guide member attached to the ablating electrode, wherein the guide member is movable by a user independently of the support members for positioning the ablating electrode. The device may also include a tubular member defining a lumen therethrough, wherein the tubular member is configured to receive the support members within the lumen when the support members are in the collapsed position.

The support member along which the ablating electrode is slidably disposed may be a main support member, and other support members may be secondary support members that extend outwardly from the main support member. The secondary support members may be independently movable about a connection point from which each secondary support member extends, and the connection point may be disposed between the main support member and the respective secondary support member.

In some embodiments, each secondary support member may comprise a support pad, wherein the support pad defines a containment dome configured to apply a vacuum to a corresponding area of the epicardium for holding the respective support pad thereto. The mapping electrodes disposed on the secondary support members may be disposed proximate a periphery of the respective support pad. In some cases, the containment dome may be configured to receive a needle electrode therethrough, wherein the needle electrode is configured to penetrate a thickness of a cardiac wall. The needle electrode may be configured to receive electrical impulses from a corresponding region within the cardiac wall during a mapping procedure and to transmit energy to the corresponding region within the cardiac wall during an ablation procedure. Furthermore, the main support member may define a first tubing portion and a second tubing portion, wherein the first tubing portion extends from a vacuum source and is in fluid communication with each containment dome, and wherein the second tubing portion is configured to receive a guide member therethrough. The guide member may be movable by a user independently of the main support member for positioning the ablating electrode with respect to the main support member. In some embodiments, a contact surface of the main support member may define a guide channel along which the ablating electrode is movable.

At least some electrodes may be configured to transmit energy independently of other electrodes during the ablation procedure. Additionally or alternatively, at least one electrode may be configured to transmit an electrical impulse for a predetermined period of time at a predetermined voltage during a pacing procedure.

In still other embodiments, a medical device for treating cardiac arrhythmias is provided that includes a main support member, at least one secondary support member extending outwardly from the main support member, and at least one electrode configured to receive electrical impulses disposed on each secondary support member. The secondary support member may comprise a support pad configured to be removably attached to a corresponding area of the epicardium for holding the medical device in place during a procedure.

The support pad may define a containment dome configured to apply a vacuum to a corresponding area of the epicardium for holding the respective support pad thereto. Additionally or alternatively, at least one electrode may be configured to receive electrical impulses from or transmit energy to a target site proximate the electrode, wherein the at least one electrode is slidably disposed along the main support member. The medical device may be configured to be collapsed about the main support member for delivery to a target site.

In still other embodiments, a method of treating cardiac arrhythmias is provided that includes making an incision in a thoracic area of a patient's body and collapsing a medical device for insertion through the incision. The medical device may comprise a main support member; at least one secondary support member extending outwardly from the main support member, each secondary support member comprising a support pad; and at least one electrode configured to receive electrical impulses disposed on each secondary support member.

The method may further include advancing the medical device in a collapsed position to a target site on an epicardium of the heart, expanding the medical device proximate the target site, and removably attaching each support pad of the secondary support member to a corresponding area of the epicardium.

In some cases, the support pad may define a containment dome, and the method may further comprise applying a vacuum to the corresponding area of the epicardium for holding the respective support pad thereto. Additionally or alternatively, the medical device may further comprise at least one ablating electrode configured to transmit energy to a target site proximate the electrode that is slidably disposed along the main support member, and the method may further comprise moving the ablating electrode with respect to the main support member and ablating portions of cardiac tissue via the ablating electrode.

BRIEF DESCRIPTION OF THE DRAWINGS

Figures 2, 2A:
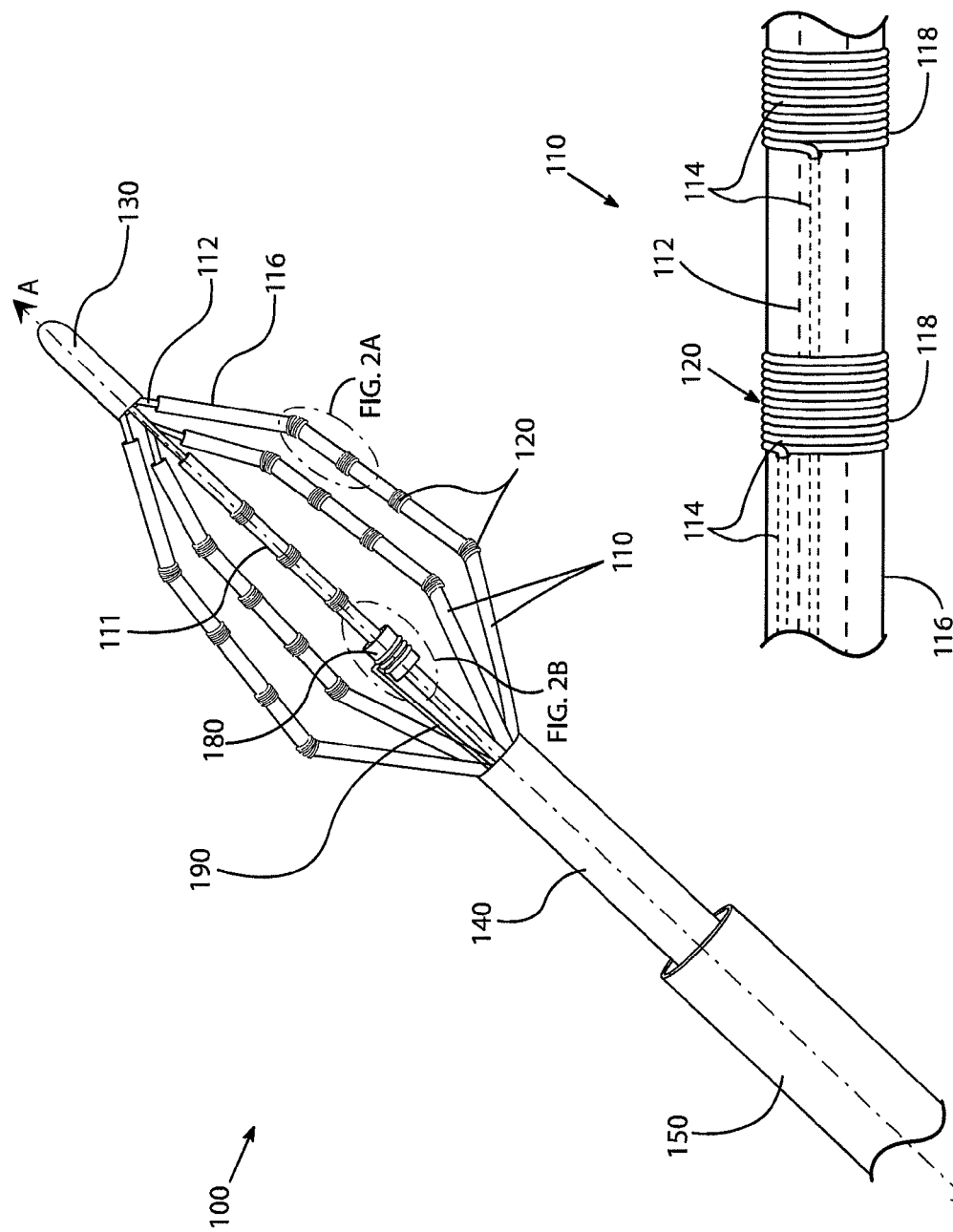
Figure 2B:
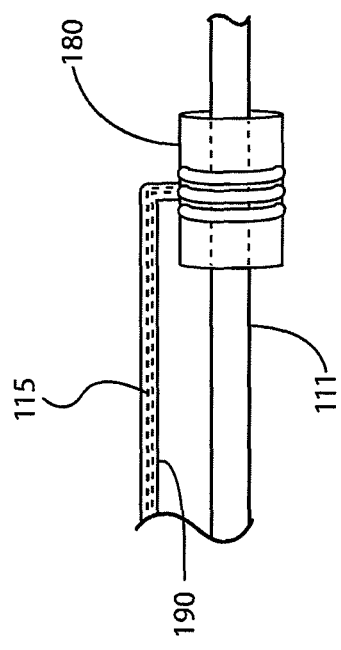
Figure 3:
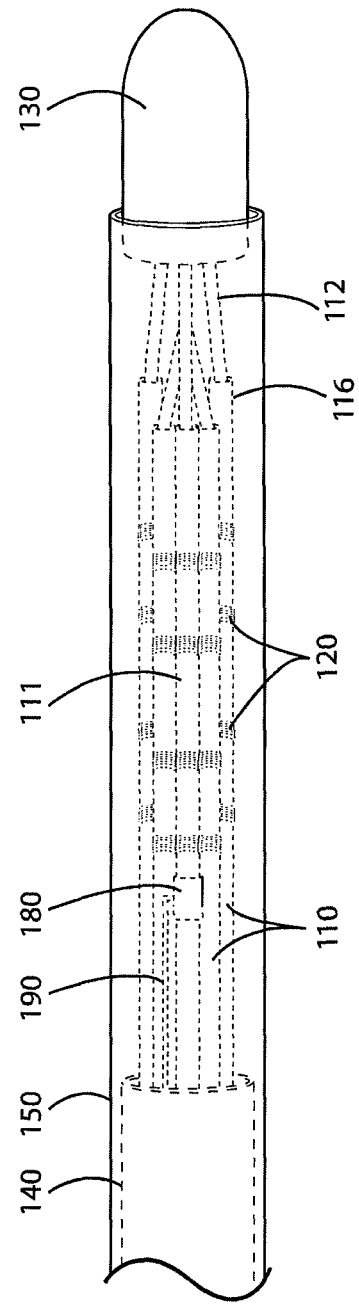
Figure 4:
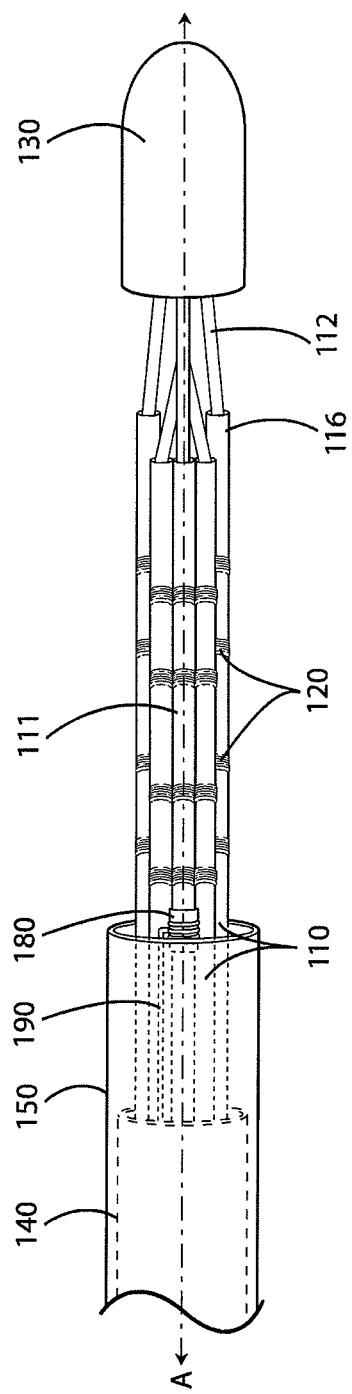
Figure 5:
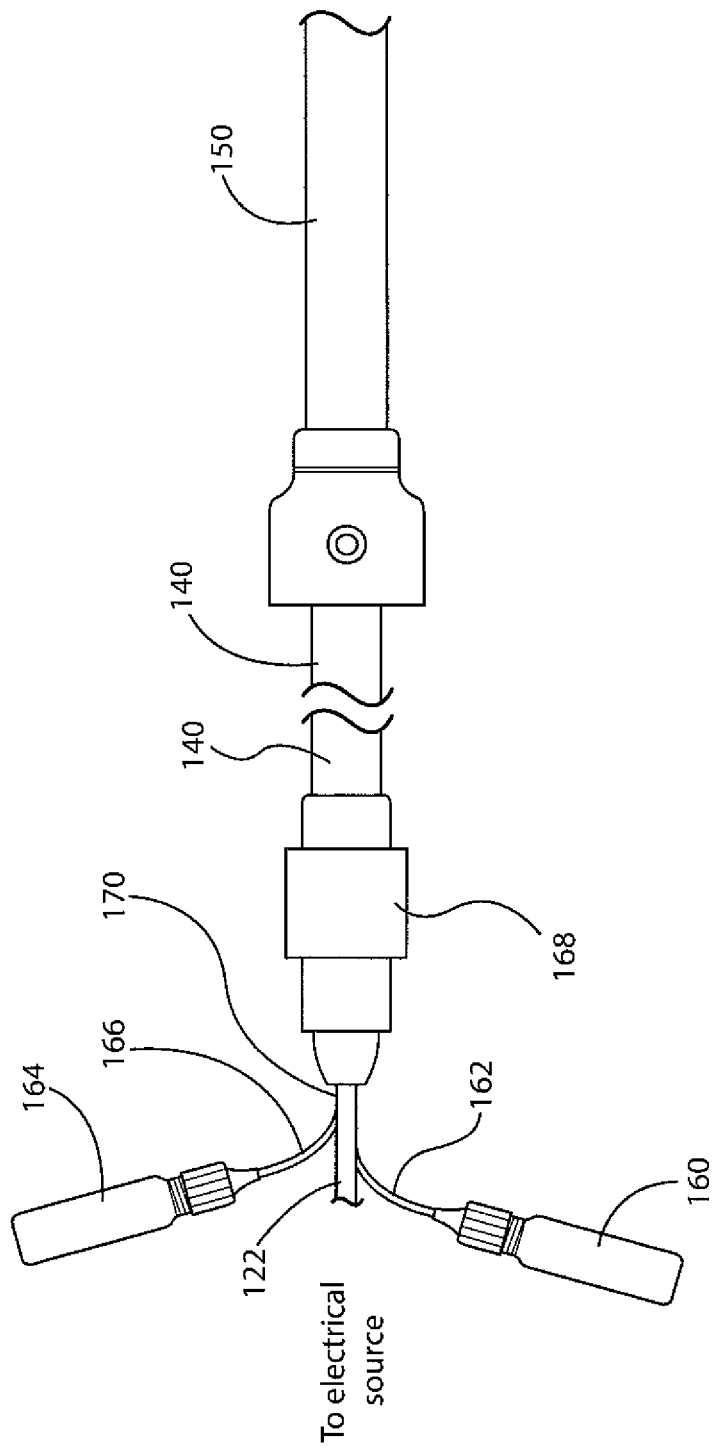
Figure 6:
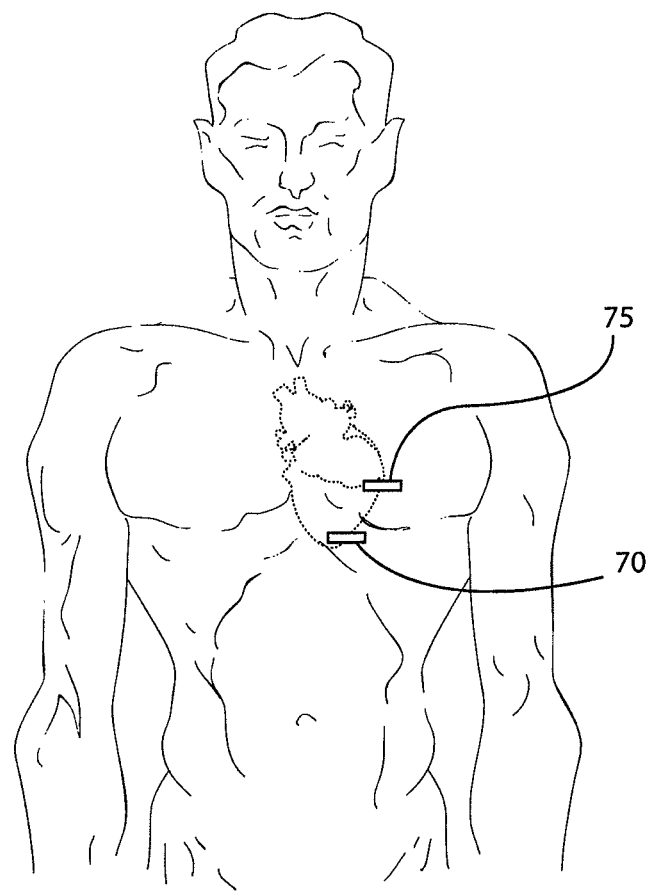
Figure 15:
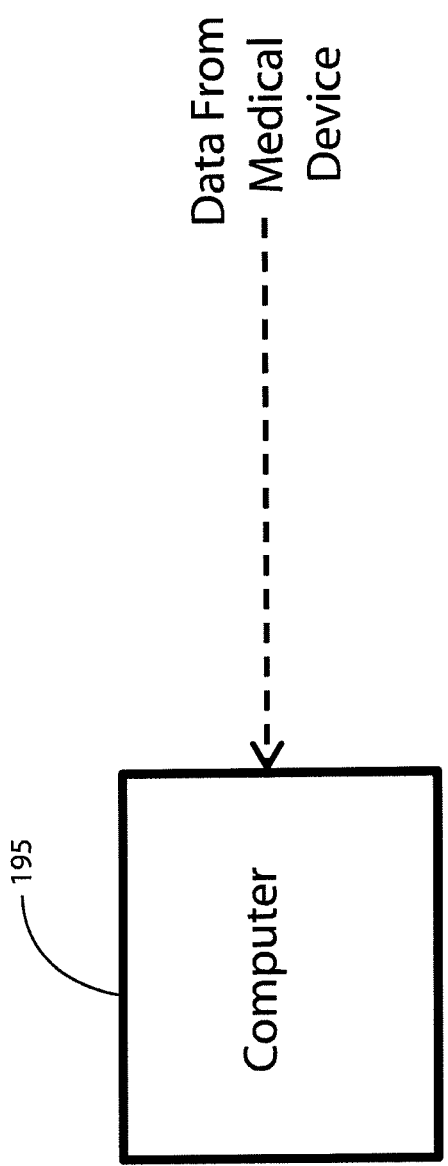
Figure 16:
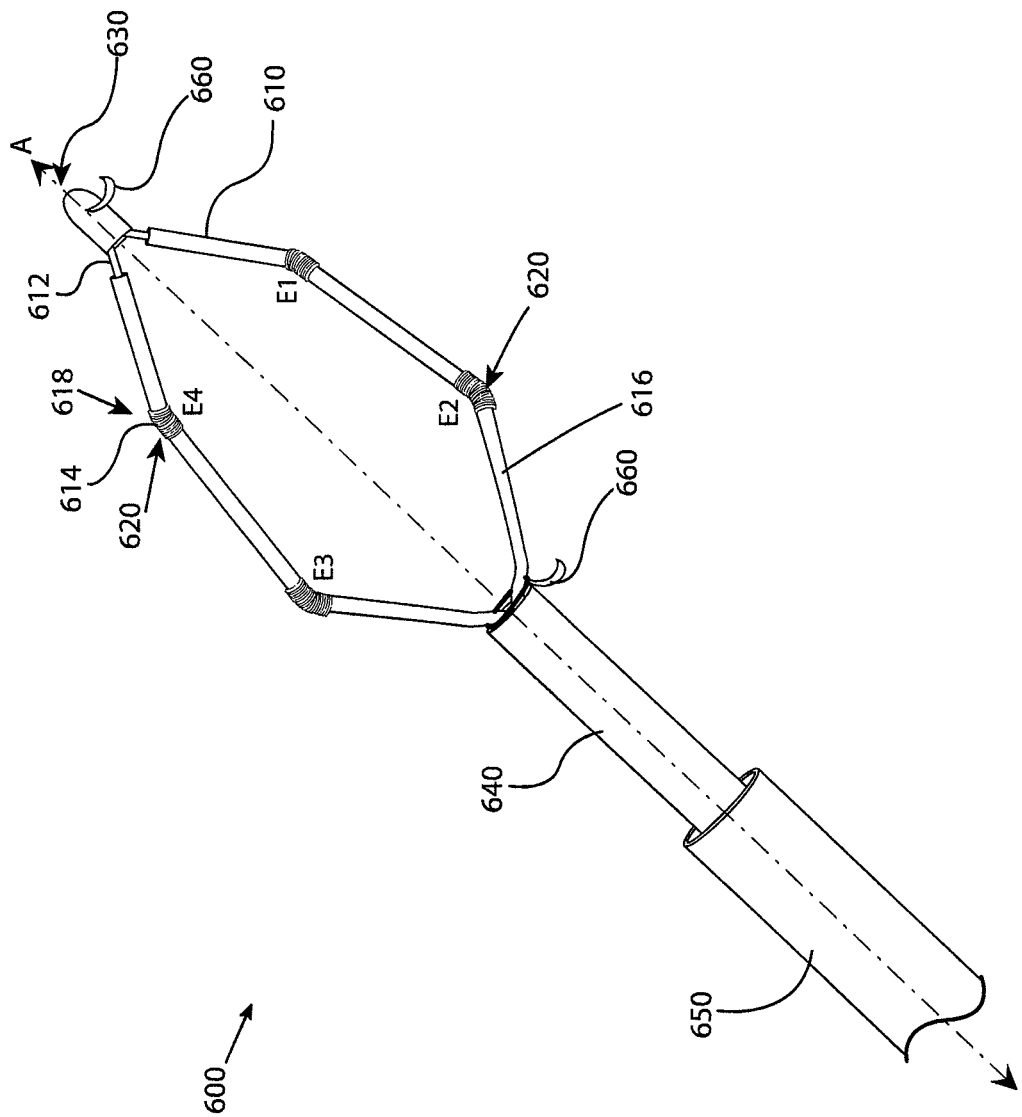
Figure 17:
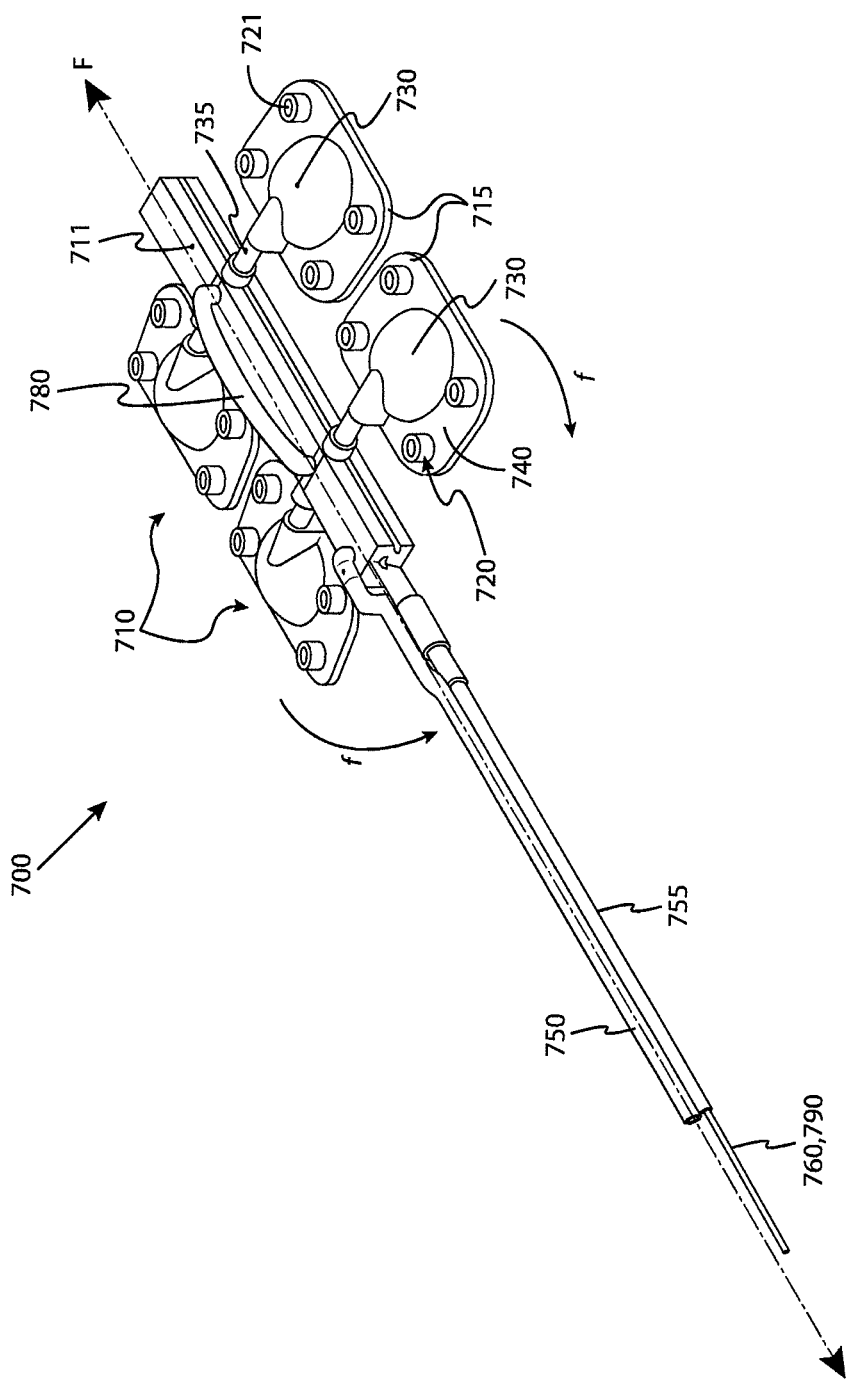
Figure 18:
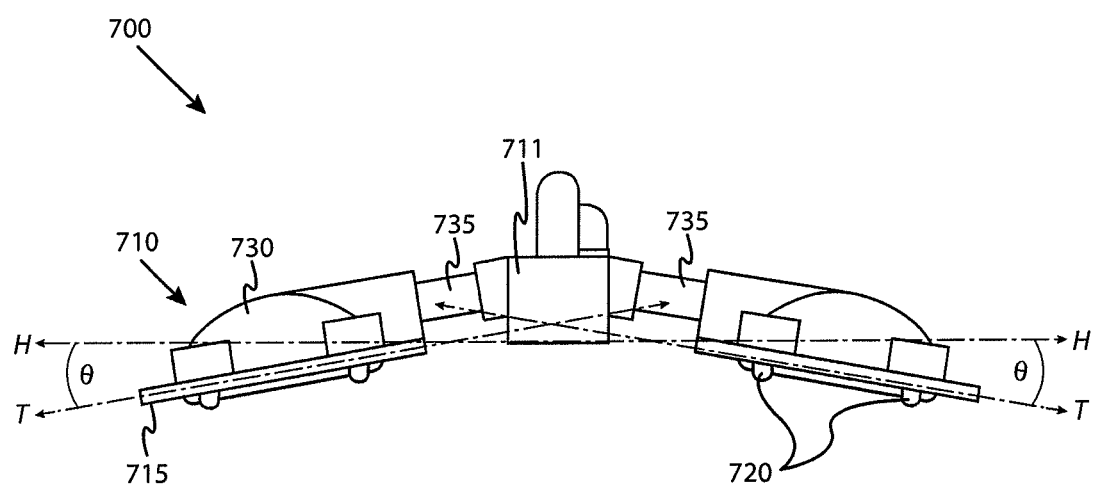
Figure 19:
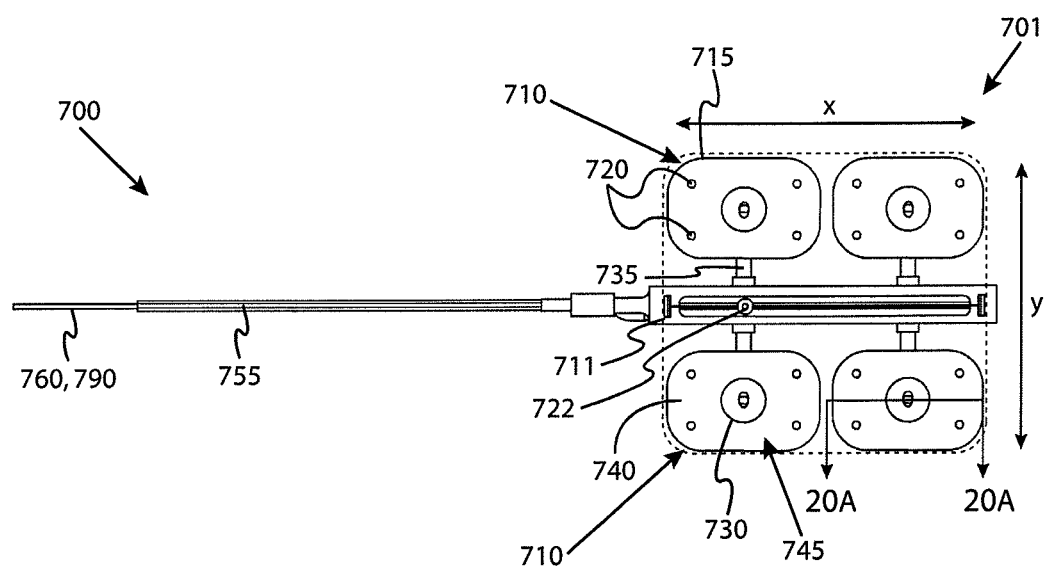
Figure 20A:
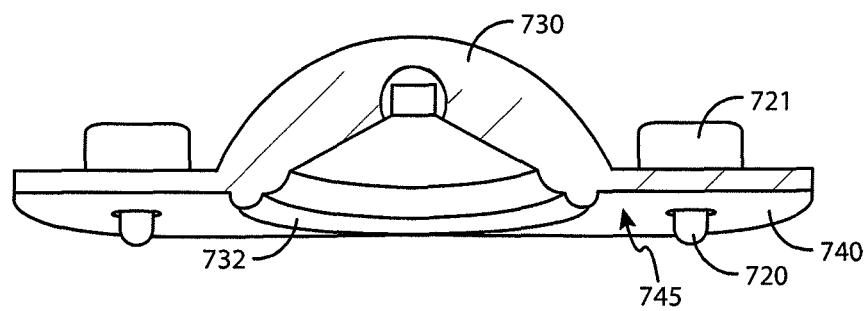
Figure 20B:
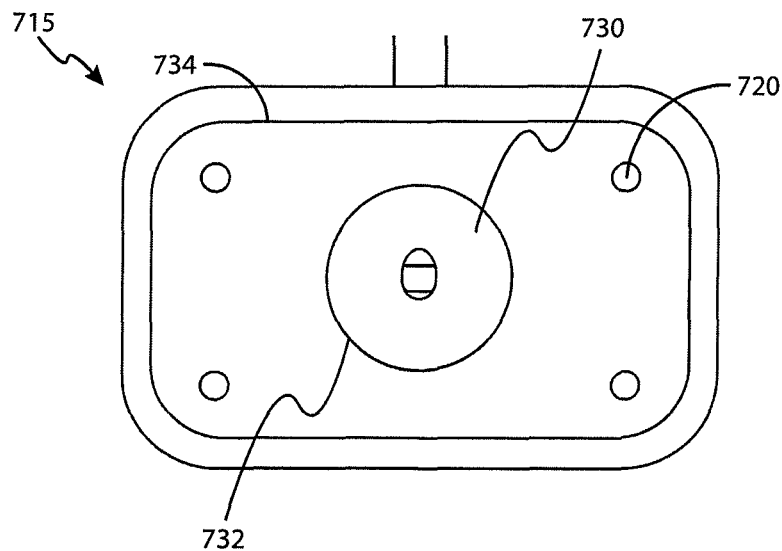
Figure 21:
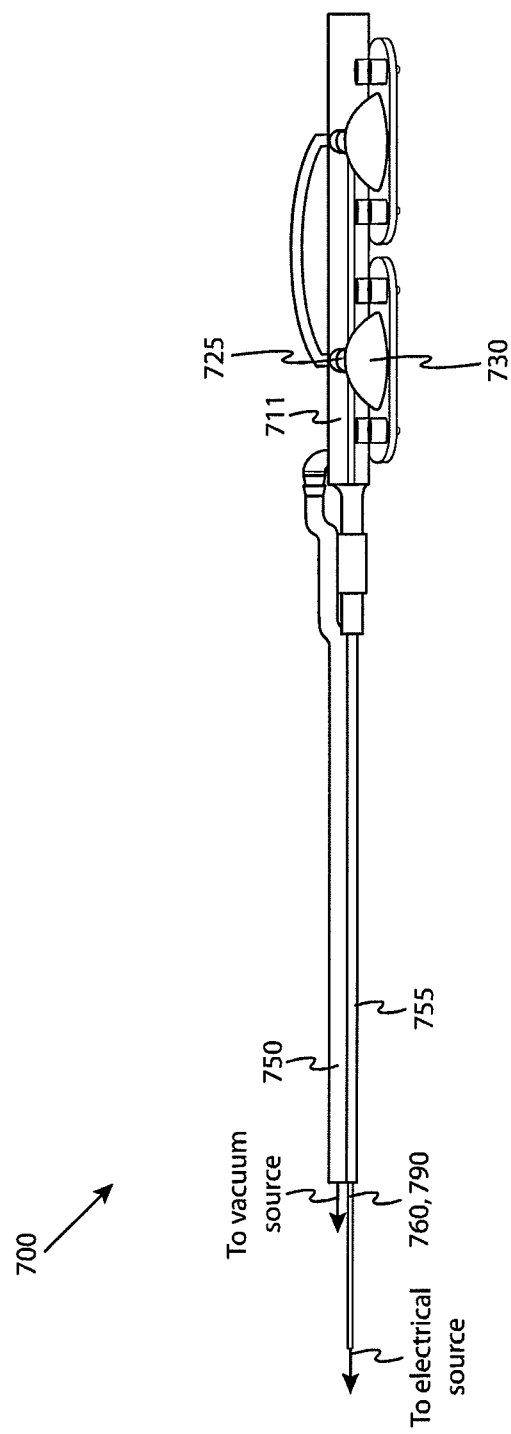
Figure 22:
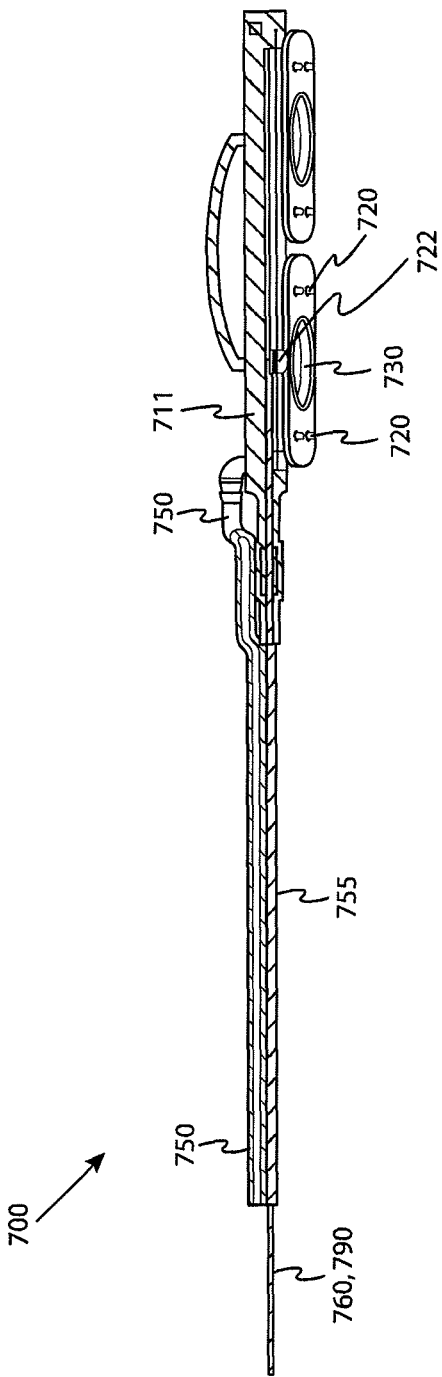
Figure 23:
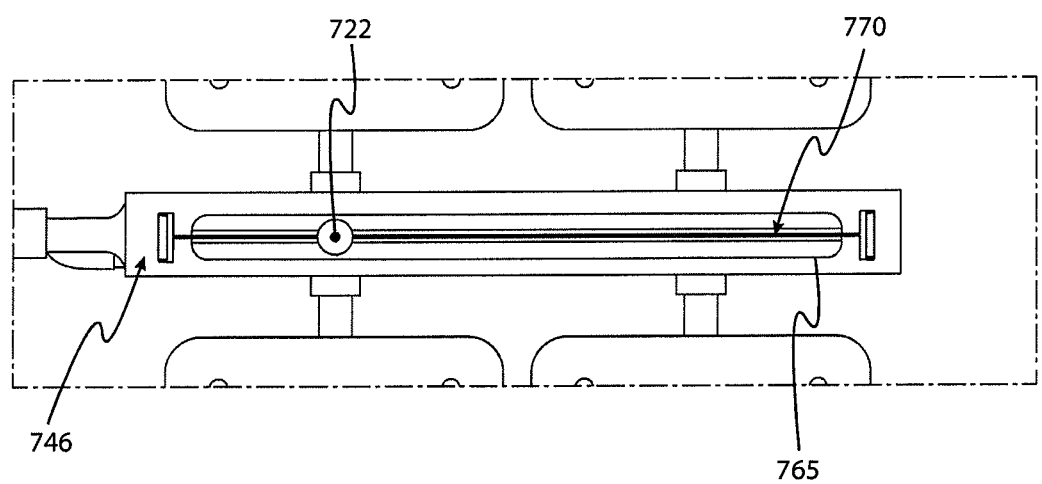
Figure 24:
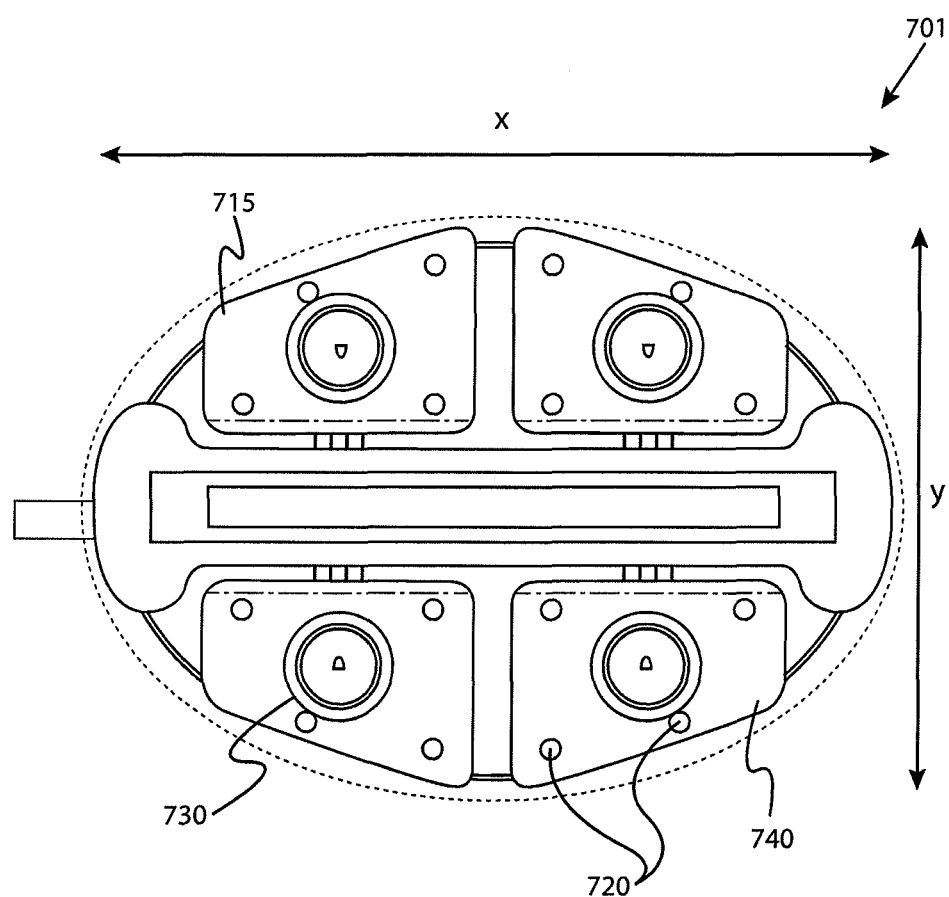
Figure 25:
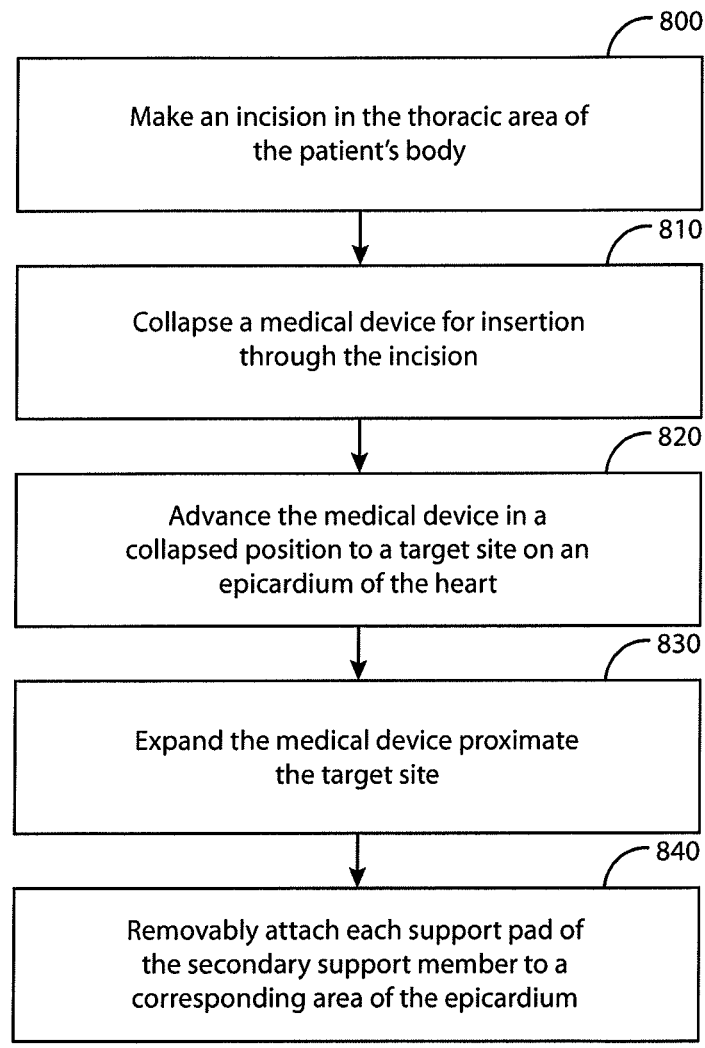

Having thus described the invention in general terms, reference will now be made to the accompanying drawings, which are not necessarily drawn to scale, and wherein:

FIG. 1 shows a schematic representation of a human heart;

FIG. 1A shows a schematic representation of layers of a portion of the cardiac wall of the heart of FIG. 1;

FIG. 2 illustrates a side view of a medical device in an expanded configuration in accordance with an exemplary embodiment of the present invention;

FIG. 2A illustrates a close-up view of a mapping electrode of the medical device of FIG. 2 in accordance with an exemplary embodiment of the present invention;

FIG. 2B illustrates a close-up view of an ablating electrode of the medical device of FIG. 2 in accordance with an exemplary embodiment of the present invention;

FIG. 3 illustrates a side view of the medical device of FIG. 2 in a collapsed configuration in accordance with an exemplary embodiment of the present invention;

FIG. 4 illustrates a side view of the medical device of FIG. 2 in a configuration between the expanded configuration of FIG. 2 and the collapsed configuration of FIG. 3 in accordance with an exemplary embodiment of the present invention;

FIG. 5 illustrates a proximal end of the medical device of FIG. 2 in accordance with an exemplary embodiment of the present invention;

FIG. 6 shows a schematic representation of a human torso including incisions for inserting and delivering a medical device and an optical device in accordance with an exemplary embodiment of the present invention;

FIG. 7 illustrates a side view of a medical device in accordance with another exemplary embodiment of the present invention;

FIG. 8 illustrates a side view of the medical device of FIG. 7 inserted into the cardiac wall in accordance with an exemplary embodiment of the present invention;

FIG. 9 illustrates a side view of a medical device in accordance with another exemplary embodiment of the present invention;

FIG. 10 illustrates a side view of the medical device of FIG. 9 with the mapping electrode in an extended position in accordance with an exemplary embodiment of the present invention;

FIG. 11 illustrates a side view of the medical device of FIG. 9 with the ablating electrodes in an extended position in accordance with an exemplary embodiment of the present invention;

FIG. 12 illustrates a side view of a medical device in accordance with another exemplary embodiment of the present invention, with the mapping electrode penetrating the cardiac wall;

FIG. 13 illustrates a side view of the medical device of FIG. 12 in accordance with an exemplary embodiment of the present invention, with the mapping electrode and the ablating electrodes penetrating the cardiac wall;

FIG. 14 illustrates a side view of a containment device used in conjunction with the medical device of FIG. 12 in accordance with another exemplary embodiment of the present invention;

FIG. 15 illustrates a schematic representation of a system configured to allow for the analysis of data;

FIG. 16 illustrates a side view of a medical device for pacing applications in an expanded configuration in accordance with an exemplary embodiment of the present invention;

FIG. 17 illustrates a perspective view of a medical device in accordance with another exemplary embodiment of the present invention;

FIG. 18 illustrates a side view of the medical device of FIG. 17 in accordance with another exemplary embodiment of the present invention;

FIG. 19 illustrates a plan view of the medical device of FIG. 17 from a contact surface side of the device in accordance with another exemplary embodiment of the present invention;

FIG. 20A illustrates a cross-sectional view of a support pad of the medical device of FIG. 19 in accordance with another exemplary embodiment of the present invention;

FIG. 20B illustrates a close-up view of one of the support pads of the medical device of FIG. 19 in accordance with another exemplary embodiment of the present invention;

FIG. 21 illustrates a side view of the medical device of FIG. 17 in accordance with another exemplary embodiment of the present invention;

FIG. 22 illustrates a cross-sectional view of the medical device of FIG. 21 in accordance with another exemplary embodiment of the present invention;

FIG. 23 illustrates a close-up view of the main support member of the medical device of FIG. 19 in accordance with another exemplary embodiment of the present invention;

FIG. 24 illustrates a plan view of a medical device from a contact surface side of the device in accordance with another exemplary embodiment of the present invention; and FIG. 25 illustrates a flowchart of a method for treating cardiac arrhythmias in accordance with another exemplary embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "distal" and "distally" refer to a location farthest from the user of a medical device (e.g., the surgeon); the terms "proximal" and "proximally" refer to a location closest to the user of the medical device. Furthermore, although each example described herein refers to treatment of cardiac tissue, embodiments of the described invention may be used to treat tissue abnormalities in various locations.

Referring now to FIG. 1, a schematic representation of a human heart 10 is shown, with a close-up view of a portion of the cardiac wall provided in FIG. 1A to illustrate the different layers of the cardiac wall. As shown in FIG. 1A, the cardiac wall 20 is made up of three layers: the pericardium 30 (the outermost layer), the myocardium 40 (the middle layer), and the endocardium 50 (the innermost layer). The pericardium 30 is a double-walled sac that contains the heart and the roots of the major vessels leaving or entering the heart. The outer layer of the pericardium 30 is known as the parietal pericardium 32, and the inner layer of the pericardium is known as the visceral pericardium, or epicardium 34. Between the parietal pericardium 32 and the epicardium 34 is the pericardial space 36, which holds pericardial fluid and functions to reduce the friction caused by the beating and movement of the heart. The myocardium 40 is the basic muscle that makes up the heart. Electrical impulses generated elsewhere in the heart normally cause the myocardium 40 to contract periodically to pump blood into and out of the chambers of the heart. The endocardium 50 is a thin, smooth layer of epithelial tissue that lines the inner surface of all the heart chambers and valves and secretes hormones for contraction of the myocardium 40.

As noted above, cardiac arrhythmias occur when irregular or improper electrical impulses cause certain portions of the cardiac wall to contract abnormally. In serious cases of arrhythmias, such as when medication is not effective at regulating the impulses, when medication is not tolerated by the patient, or when there is a high risk of complications from the arrhythmia (e.g., sudden cardiac arrest), cardiac ablation may be used to destroy certain portions of cardiac tissue that are suspected of triggering an abnormal heart rhythm or conducting abnormal electrical signals. The cardiac tissue may, for example, be destroyed by heating the tissue (such as through the targeted application of radio frequency signals), using a laser, or through cryoablation (extreme cold).

In preparation for an ablation procedure, the electrical impulses in various locations of the heart may be mapped during an electrophysiological study in an effort to identify the areas that are causing or contributing to the arrhythmia. A typical mapping procedure may involve the insertion of mapping catheters into a patient's vein (such as a vein in the groin, neck, or forearm). The mapping catheter may then be advanced to various locations of the heart.

Once the origin of the arrhythmia is located, another catheter (an ablation catheter) may be intravenously advanced to the target site. A dye may be injected through the catheter to allow the user (e.g., the surgeon) to monitor the location of the distal end of the ablation catheter using X-ray images as the catheter is positioned at the target site.

Conventional mapping and ablation procedures have many shortcomings. When catheters are used to intravenously identify and treat a target site, only abnormalities in the endocardium 50 can be detected and addressed because the distal end of the catheter is advanced, through the vein, to each chamber of the heart (e.g., from the inside of the heart). Abnormalities may occur in any of the layers of the cardiac wall, however, and as such defects in the myocardium 40 and the epicardium 34, for example, may go undetected and untreated.

In addition, the constant beating of the heart creates an unstable and uncontrolled environment in which the user of the mapping catheter and the ablation catheter must operate. The ebb and flow of blood in the vein through which the catheter is advanced may cause the position of the distal end of the catheter to move, both during mapping and ablation procedures. As such, accurate positioning of the distal end is made very difficult, and the movement of the heart muscle itself with each contraction may make maintaining the proper position of the distal end with respect to the target site difficult. As a result, data recorded during a mapping procedure may not accurately correlate the detected electrical activity with a particular area of the endocardium, and the ablation of cardiac tissue during an ablation procedure may not address the correct location or may cover too large an area (thereby destroying good tissue along with abnormal tissue), for example. Also, too much or too little energy may be used for the ablation, thus destroying a portion of the tissue that is either too deep (again destroying good tissue) or not deep enough (making the procedure partially or completely ineffective). Moreover, the images provided via X-ray only offer the user an indirect way to monitor the location of the catheter and may not provide the user with a clear and focused picture of the target area, thereby adding to the challenges.

In some cases, the heart may not be contracting at the right times or with enough strength to produce adequate pumping action. For example, although a healthy heart may be able to achieve 60% ejection of blood with its pumping, a weak or unhealthy heart may only be able to achieve 20% ejection, which compromises the health of downstream tissue and organs. Accordingly, artificial pacing devices may be used to provide the heart with artificial electrical stimulus to encourage effective pumping action.

In many cases, it may be necessary to pace both the left and right sides of the heart to mimic the natural pacing of the heart and coordinate the function between the atria and ventricles. Conventional pacing devices are typically inserted transvenously through the coronary sinus and passed into the right ventricle. The left side of the heart may be approached epicardially, for example via a thoracotomy; however, conventional devices and methods of installing artificial pacemakers do not provide an effective way to provide permanent pacing of various locations of the epicardial surface in a minimally invasive manner.

Accordingly, embodiments of the present invention provide devices, systems, and methods for treating cardiac arrhythmias epicardially (e.g., approaching the target site from outside the heart rather than from within one of the chambers) while still allowing the procedure to be conducted in a minimally-invasive manner, such as orthoscopically, as opposed to via a thoracotomy or mini-thoracotomy. In this way, abnormal electrical impulses may be mapped in any layer of the cardiac wall (e.g., in the epicardium 34, the myocardium 40, and/or the endocardium 50), and the medical device may be accurately positioned and maintained at the identified target site to ablate the correct location and amount of defective tissue (coverage area and depth). Additionally or alternatively, artificial pacing may be provided on a permanent basis anywhere on the epicardial surface of the heart.

One embodiment of a medical device for treating cardiac arrhythmias is shown in FIGS. 2-5. With reference to FIG. 2, the depicted embodiment of the medical device 100 comprises a plurality of support members 110 that are configured to be moved between an expanded position (shown in FIG. 2) and a collapsed position (shown in FIG. 3), as described in greater detail below. At least one mapping electrode 120 may be disposed along each support member 110, and the mapping electrode may be configured to receive electrical impulses such that the electrophysiology of the region of the heart proximate the mapping electrodes may be recorded and analyzed to identify abnormalities associated with the cardiac arrhythmia.

In the depicted embodiment, for example, the medical device 100 includes five support members 110, although a greater or smaller number of support members may be provided. Referring to FIGS. 2 and 2A, each support member 110 may have a central wire 112 made of a generally non-conductive material or a conductive metal having an insulated sheath, such as insulated stainless steel or other insulated metals, including metals with shape memory properties such as nitinol, that provides rigidity and structure to the support member in the expanded position, while allowing the support member the flexibility to be moved between the expanded position of FIG. 2 and the collapsed position of FIG. 3. In some cases, a polymeric material or a shape memory alloy, such as nitinol, may be used as the central wire 112, and the central wire may have a predefined shape (e.g., may be pre-bent at one or more locations, as shown) such that, when unconstrained in the expanded position as depicted in FIG. 2, the central wire may urge the support member 110 to assume an expanded configuration by virtue of the wire's shape memory properties, for example, as shown.

With reference to FIG. 2A, which illustrates a detail view of a portion of a support member 110, a conductive element 114 (e.g., a silver or platinum wire) may be extended from an electrical source (not shown) towards a distal end 130 of the medical device 100 within an insulating sheath 116. An opening 118 may be defined in the sheath 116 (which may, for example, be made of a polymeric material), and the conductive element 114 may be passed through the opening from within the sheath and wrapped around the sheath to form the mapping electrode 120. Thus, in the depicted embodiment, in which each support member 110 has four mapping electrodes 120 disposed thereon, four openings 118 may be defined in the sheath 116 at locations corresponding to the locations of the mapping electrodes, and four conductive elements 114 may be extended through the sheath from the electrical source to each opening for a particular support member. In other embodiments, the mapping electrodes may be formed of a solid metal portion or a metal ring disposed around the sheath at the corresponding locations.

In some embodiments, a connecting member 140 may be disposed about the support members 110 proximally of distal end 130, such that a distal end of the connecting member defines a proximal end of the support members, as shown. In other words, the support members 110 in the depicted embodiment may extend between the connecting member 140 and the distal end 130 of the medical device 100 (the distal end 130, for example, being defined by an end cap, electrical tape, or some other structure configured to hold together the distal ends of the support members to form a cohesive and unitary end of the medical device). The connecting member 140 may be, for example, a sheath, coating, electrical tape, or other structure that is attached to at least some of the support members 110 and holds the proximal ends of the support members together. In some embodiments, however, one or more of the support members 110 may be at least partially movable independently of others of the support members and/or independently of the connecting member 140 to allow for the configuration of the support members to be adjusted in the expanded position, as described below.

Continuing to refer to FIG. 2, the array of mapping electrodes 120 provided on the support members 110 in the expanded position may allow electrophysiological data to be collected over a surface of epicardium 34 (FIG. 1A), with each mapping electrode 120 receiving electrical impulse data from a location on the epicardium corresponding to the location of the mapping electrode.

As noted above, the support members 110 may be configured to be moved between the expanded position (FIG. 2) and a collapsed position (FIG. 3). In this regard, the medical device 100 may further include a tubular member 150 that defines a lumen therethrough. The tubular member 150 may be configured to receive the support members 110 within the lumen when the support members are in the collapsed position. For example, retraction of the support members 110 via the connecting member 140 into the tubular member 150 (e.g., by moving an extension of the connecting member provided at an operator-side of the medical device, as explained below, proximally relative to the tubular member) may apply a radial constraint on the support members and may thus cause the support members 110 to move towards a central axis A of the medical device 100, as shown in FIG. 4. In this way, the connecting member 140, the support members 110, and the distal end 130 or a portion of the distal end 130 may be received within the tubular member 150, as shown in FIG. 3.

Accordingly, during a mapping procedure, the user (e.g., a surgeon) may make a small incision in the patient's thoracic region and may insert the distal end 130 of the medical device 100 into the incision and advance the medical device to the patient's pericardial space 36 (FIG. 1A). Once the distal end 130 is in a desired location, the user may move the support members 110 from the collapsed position (FIG. 3) to the expanded position (FIG. 2) by moving the tubular member 150 distally with respect to the connecting member 140 and the support members. The removal of the tubular member 150 from around the support members 110, as described above, then allows the support members to be moved towards the expanded position (FIG. 2).

Referring now to FIG. 5, in some cases, a first handle 160 may be provided at a proximal end 170 of the medical device 100 for adjusting the configuration of the support members 110. The first handle 160 may, for example, be attached to a first pusher member 162, such as a wire or other elongate member that extends from the proximal end 170 of the medical device to one of the support members 110. In some cases, the first pusher member 162 may be one of the central wires 112 shown in FIG. 2 that forms the structure of one of the support members 110. For example, in the configuration of the medical device 100 shown in FIG. 2, in which a central support member 111 is provided with two additional support members on either side of the central support member, the central wire 112 forming the central support member may serve as or be attached to the first pusher member 162.

Accordingly, once the support members 110 are withdrawn from the tubular member 150, as shown in FIG. 2, a user may expand or further expand the configuration of the support members to achieve the desired coverage for mapping of a particular surface area of the epicardium by moving the first pusher member 162 (e.g., via the first handle 160) distally with respect to the connecting member 140. In other words, in some embodiments, the exposed length of the central support member 111 may be "shortened" by retracting a portion of the central support member back into the connecting member 140 via relative proximal movement of the first handle 160, such that the other support members (which may be fixed to the connecting member 140) are moved away from the central axis A of the medical device 10 and provide a greater coverage area of the mapping electrodes.

In some cases, an optical device, such as a fiber optic camera, may be advanced to the patient's pericardial space to allow the user to visually monitor the position of the distal end 130 of the medical device 100 with respect to the location of the heart to be mapped. For example, as shown in FIG. 6, a first incision 70 may be made in the thoracic area of the patient's body, and a distal end of the medical device may be inserted into the first incision 70 and positioned proximate the area of the epicardium to be mapped. A second incision 75 may also be made in the thoracic area of the patient's body, and an optical device (such as a fiber optic camera) may be advanced to a location near the distal end of the medical device. In some cases, the optical device may form part of the medical device 100 itself, such as via an attachment to the distal end of the medical device rather than a separate device. The optical device may be configured to capture and transmit an epicardial view of the cardiac tissue (e.g., a view of the heart taken from the pericardial space). Using the epicardial view, the user may be able to position the distal end 130 of the medical device 100 proximate the desired location (e.g., the target site), and the electrical impulses received from the target site may be mapped via the mapping electrodes 120 provided on the support members 110.

Once an appropriate surface of the epicardium is mapped and analyzed, and the user has identified a target site for ablation, the medical device 100 illustrated in FIGS. 2-5 may further be used to ablate epicardial tissue. Referring again to FIG. 2, the medical device 100 may further include an ablating electrode 180 that is slidably disposed on one of the support members 110, such as on the central support member 111. The ablating electrode 180 may be, for example, a cylindrical element made of a conductive material that is disposed around the respective support member (e.g., the central support member 111). A guide member 190, such as a wire, may be provided that is attached to the ablating electrode 180, as shown in FIGS. 2A and 2B, and may extend from the ablating electrode and into the connecting member 140.

Referring to FIG. 5, a second handle 164 may be provided at the proximal end 170 of the medical device 100 that is attached to a second pusher member 166 configured to axially move the ablating electrode 180 via movement of the guide member 190. The guide member 190 may, in some cases, be attached to the second pusher member 166 (e.g., at a location within the connecting member 140), or, in other cases, the guide member may serve as the second pusher member.

The ablating electrode 180 may be configured to transmit energy, such as radio frequency (RF) energy, to a target site proximate the ablating electrode via a conductive element 115, shown in FIG. 2B, that is connected to the electrical source (not shown). The conductive element 115 may be supported by the guide member 190, for example, being wrapped around or extending along the guide member. The conductive element 115 providing the ablating electrode 180 with access to the electrical source and the conductive elements 114 providing the mapping electrodes with access to the electrical source may be bundled together within an insulating sheath 122 extending to the electrical source, as shown in FIG. 5.

The data received by the mapping electrodes 120 may be accessed and analyzed by the operator or other trained medical personnel (such as an electrophysiologist) via a computer 195, as shown in FIG. 15. The computer 195 or other device including a processor and a display for receiving and enabling analysis of the data may be co-located with the patient (e.g., in the same operating room), or, in some cases, the data may be transmitted to a remote location for analysis, such as when the person analyzing the data is located remotely from the operator of the medical device and the data is transmitted to the remote location via the Internet or intranet. Thus, in some cases, more than one computer may be used to allow for the analysis of the data. Moreover, the computer 195 or other processing device may be used to analyze other data received from the medical device or peripheral devices, including the optical device.

Accordingly, in the embodiment depicted in FIGS. 2-5, once an epicardial surface of the heart has been mapped by positioning the medical device 100 at a particular location, expanding the support members 110, and receiving electrical impulses via the mapping electrodes 120 over a particular coverage area, a target site for an ablation procedure may be identified. The support members 110, and in particular the central support member 111 about which the ablating electrode 180 is disposed, may then be positioned proximate the target site, and the ablation procedure may be initiated. As the ablating electrode 180 transmits energy (e.g., RF energy) to the adjacent tissue to heat and destroy the abnormal tissue, the guide member 190 may be moved by the user via the second handle 164 and/or the second pusher member 166 to thereby move the ablating electrode 180. Movement of the ablating electrode 180 may, in some embodiments, form a line of ablation at the target site (e.g., on the adjacent cardiac tissue of the epicardium). Furthermore, by monitoring the position of the distal end 130 of the device 100 using a fiber optic camera, as described above, the position of the device may be adjusted via manipulation of a main handle 168 to reposition the ablating electrode 180 and form additional linear ablations, as needed.

Although mapping and ablating procedures are primarily described above in the context of the figures and examples provided, embodiments of the medical devices 100, 200, may also be configured to perform pacing procedures. Accordingly, for example, each electrode may also be configured to transmit an electrical impulse for a predetermined period of time at a predetermined voltage during a pacing procedure. This may be done as a temporary measure, such as to stimulate the heart with electrical activity if necessary during a mapping or ablating procedure. In other cases, the medical device may be configured to be permanently installed in the cardiac wall, such as by configuring the device to receive wireless energy transmissions from a location outside the patient's body, and may function as a permanent pacing device. In still other cases, embodiments of the pacing device described below may be used during a bypass or a valve procedure for patients undergoing heart surgery as a screening tool or for research purposes in an attempt to identify patients who may be at risk for arrhythmias post-operatively, even if they haven't experienced such trouble before.

For example, with reference to FIG. 16, a medical device 600 may be provided that includes two support members 610, although a greater or smaller number of support members may be provided. As described above with respect to the medical device 100 for ablation, each support member 610 may have a central wire 612 made of a generally non-conductive material or a conductive metal having an insulated sheath, such as insulated stainless steel or other insulated metals, including metals with shape memory properties such as nitinol, that provides rigidity and structure to the support member in the expanded position, while allowing the support member the flexibility to be moved between the expanded position of FIG. 16 and the collapsed position (e.g., as shown in FIG. 3). In some cases, a polymeric material or a shape memory alloy, such as nitinol, may be used as the central wire 612, and the central wire may have a predefined shape (e.g., may be pre-bent at one or more locations, as shown) such that, when unconstrained in the expanded position as depicted in FIG. 16, the central wire may urge the support member 610 to assume an expanded configuration by virtue of the wire's shape memory properties, for example, as shown.

As described above with reference to FIG. 2A and with continued reference to FIG. 16, a conductive element (e.g., a silver or platinum wire) may be extended from an electrical source (not shown) towards a distal end 630 of the medical device 600 within an insulating sheath 616. An opening 618 may be defined in the sheath 616 (which may, for example, be made of a polymeric material), and the conductive element 614 may be passed through the opening from within the sheath and wrapped around the sheath to form the pacing electrode 620. Thus, in the depicted embodiment, in which each support member 610 has two pacing electrodes 620 disposed thereon, two openings 618 may be defined in each sheath 616 at locations corresponding to the locations of the pacing electrodes, and two conductive elements 612 may be extended through each sheath from the electrical source to each opening for a particular support member. In other embodiments, the pacing electrodes may be formed of a solid metal portion or a metal ring disposed around the sheath at the corresponding locations.

In some embodiments, a connecting member 640 may be disposed about the support members 610 proximally of the distal end 630 of the device 600, such that a distal end of the connecting member defines a proximal end of the support members, as shown. In other words, the support members 610 in the depicted embodiment may extend between the connecting member 640 and the distal end 630 of the medical device 600. The distal end 630 may, in some cases, be defined by an end cap, electrical tape, or some other structure configured to hold together the distal ends of the support members to form a cohesive and unitary end of the medical device. Furthermore, in some embodiments, the distal end 630 may comprise an attachment member 660 that is configured to secure the medical device to body tissue at the target site. The attachment member 660 may be, for example, a hook, wire, or other engaging point that hooks into the body tissue at the desired location to maintain the medical device 600 in place and allow the body tissue to grow over or otherwise incorporate the device into the tissue. In this regard, a second attachment member 660 may also be provided in some cases at the proximal end of the support members 610 to facilitate fixation of the device 600 at the target site. Thus, at least one attachment member may be disposed at an end of the support members. In still other embodiments, a plurality of attachment members 660 may be provided along the support members 610 between the connecting member 640 and the distal end 630. The attachment members 660 may be evenly distributed along the support members 610 or, in some cases, may be clustered at various locations along the support members. In some cases, at least one of the attachment members 660 may comprise a spherical or semi-spherical attachment member that includes a number of engaging points, similar to a plant bur. In other embodiments, the attachment member may comprise a sheet that is configured to be overlaid on the medical device 600 to secure the device to the heart.

In some embodiments, the attachment members 660 may be coated with a material that is configured to dissolve after exposure to bodily fluids for a predetermined amount of time for allowing the at least one attachment member to secure the medical device in place. The coating may, for example, be sugar-based and may be configured to allow the surgeon 5-10 minutes to position the device 600 before dissolving to expose the attachment members 660. In other words, while the coating is intact, the attachment members 660 may be covered and not able to attach the device to the heart muscle, whereas after the coating has dissolved (e.g., due to exposure to body fluids for a certain amount of time), the attachment members may be revealed and may be able to engage the body tissue to fix the device 600 in place.

In some embodiments, the coated attachment members 660 may be configured to fit within the connecting member 640 when the device is in the collapsed position. The connecting member 640 may be, for example, a sheath, coating, electrical tape, or other structure that is attached to at least some of the support members 610. In some embodiments, the support members 610 may be movable independently of the connecting member 640 (e.g., slidable within the connecting member) to allow for the configuration of the support members to be adjusted in the expanded position, as described below.

Accordingly, as noted above, the support members 610 may be configured to be moved between the expanded position (FIG. 16) and a collapsed position (shown in FIG. 3 with respect to a different device 100). In this regard, the medical device 600 may further include a tubular member 650 that defines a lumen therethrough. The tubular member 650 may be configured to receive the support members 610 within the lumen when the support members are in the collapsed position. For example, retraction of the support members 610 via the connecting member 640 into the tubular member 650 (e.g., by moving an extension of the connecting member provided at an operator-side of the medical device, as explained below, proximally relative to the tubular member) may apply a radial constraint on the support members and may thus cause the support members 610 to move towards a central axis A of the medical device 600. In this way, the connecting member 640, the support members 610, and the distal end 630 or a portion of the distal end 630 may be received within the tubular member 650, as shown in FIG. 3 with respect to the medical device 100.

Upon moving the connecting member 640 out of the tubular member 650 (e.g., moving the connecting member distally with respect to the tubular member), the support members 610 may be configured to self-expand from the collapsed position to the expanded position, and the pacing electrodes 620 may be placed at the target site. As noted above, once the coated attachment members 660 have been exposed to body fluids for a certain amount of time and the coating has dissolved, the attachment members 660 may hook into the body tissue, and the support members 610 and electrodes 620 may not be able to be easily moved to other locations. Upon fixation of the support members 610 and electrodes 620 at the target site within the body, the tubular member 650 and the connecting member 640 may be released from the support members 610 and be withdrawn from the body, leaving the pacing electrodes in place on an epicardial surface of the heart.

The connecting member 640 may, for example, be attached to the support members 610 via a friction fit, such that once the support members 610 are engaged with the body tissue via the attachment members 660, the connecting member 640 may be pulled proximally and detached from the support members. For example, the friction fit may be the result of a plug made of the same or similar coating that is applied to the attachment members 660, such that when the plug material has dissolved due to exposure to bodily fluids, the connecting member 640 can be pulled free from the support members 610. In other embodiments, a release mechanism may be provided at an operator side of the device, such that the operator may be able to detach the connecting member 640 from the support members 610 once the device is in place and affixed to the target site (e.g., by pulling on a wire, etc.).

The pacing device 600 may be configured in numerous ways, depending on the anatomy of the patient (e.g., child vs. adult), the location of the target site, the surgeon's preferences, and other considerations. In some embodiments, in the expanded position, the support members 610 (e.g., the portion of the medical device 600 that is permanently installed in the patient) may have an overall length of between approximately 1 inch to approximately 2 inches, such as about 1½ inches. Any number of support members and pacing electrodes may be provided. In one embodiment, for example, two support members 610 may be provided as shown in FIG. 16, and each support member may include 2 pacing electrodes having a length of approximately 2 cm to approximately 4 cm each. In addition, the attachment members 660 may be configured in any way suitable for engaging the body tissue and maintaining the device 600 affixed to the target site (e.g., despite the movement caused by the heart's pumping action). In one embodiment, for example, the attachment members 660 may be configured to achieve a depth of between approximately ⅛ inches and 3/16 inches within the body tissue to secure the device in place.

Furthermore, in some embodiments, the plurality of pacing electrodes may be configured to selectively transmit the electrical impulses for pacing. In other words, although 4 pacing electrodes 620 are shown in the depicted embodiment of FIG. 16, fewer than all 4 electrodes may be selected for providing the pacing impulses, based on the locations determined to require electrical stimulation. For example, in FIG. 16, the pacing electrodes are labeled E1, E2, E3, and E4 for explanatory purposes. In one particular scenario, the surgeon may decide that pacing impulses are required at the locations corresponding to the electrodes E1 and E3 and may thus select to activate only electrodes E1 and E3 for the pacing operation. The pacing electrodes (e.g., E1 and E3 in this example) may be controlled by a pulse generator that is configured to communicate with and direct the pacing electrodes via leads or wirelessly. The pulse generator may be installed below the subcutaneous fat of the chest wall, above the muscles and bones of the patient's chest, for example.

In some cases, the abnormal tissue may be located in other layers of the cardiac wall, such as in the myocardium and/or the endocardium, in addition to or instead of in the endocardium. Additional mapping procedures to receive electrical impulses from locations within the cardiac wall may be needed to identify abnormalities in these locations. For example, mapping of the surface of the epicardium 34 may be followed by mapping through the layers of the wall, so as to identify locations in the myocardium 40 and/or the endocardium 50 that may require ablation. In particular, mapping of the epicardium 34 using an embodiment of the medical device 100 as shown in FIGS. 2-5 and described above may identify a particular region of the epicardium as the target site. Another embodiment of the medical device 200, shown in FIGS. 7 and 8, may then be used to map electrical impulses and, if necessary, to ablate surrounding tissue through a thickness of the cardiac wall.

With reference to FIG. 7, for example, the medical device 200 may comprise a support member 210 that defines a distal tip 212 configured to penetrate a thickness of a cardiac wall (as shown in FIG. 8). A plurality of electrodes 220 may be disposed along the support member 210, as described above with respect to the mapping electrodes 120 of the medical device 100. In some cases, 3 or 4 electrodes 220 spaced about 2 mm apart may be provided, although the number of electrodes may be more or less depending on the configuration of the device and the operator's preferences, among other things. For example, the support member 210 may define a lumen therethrough, and a conductive element 222 (shown in dashed lines in FIG. 7) may extend through the lumen to the location of each electrode 220. At the location of the electrode 220, an opening may be defined in the support member 210, such that the conductive element 222 may be passed from the interior of the support member to the exterior of the support member and wrapped around the outer surface to form the electrode. In the depicted embodiment, the medical device 200 includes three electrodes 220, and thus three conductive elements 222 and three openings in the support member 210 are provided. A handle member 230 may also be provided proximally of the distal tip 212. The handle member 230, which may have a tubular configuration, may be attached to the proximal end of the support member 210, and the conductive elements 222 may be run from the electrical source (not shown) at a user end of the medical device 200 to the location of each electrode 220 via a lumen of the protective sheath. In some embodiments the handle member may comprise a polymeric material and/or may include an insulated metal material.

As shown in FIG. 8, the medical device 200 may be configured to be inserted into the cardiac wall 20 via the distal tip 212. In this regard, the support member 210 and/or the distal tip 212 may be made of a rigid material, such as stainless steel, and the distal tip 212 may form a sharp point for puncturing the cardiac wall 20, in the manner of a syringe. The support member 210 may, for example, comprise a needle ranging from 16 gauge to 22 gauge, such as an 18 gauge needle. Each electrode 220 may be configured to receive electrical impulses from a corresponding region within the cardiac wall 20 during a mapping procedure, including the epicardium 34, the myocardium 40, and/or the endocardium 50. The same medical device 200 may also be used to conduct an ablation procedure (e.g., without changing the position of the medical device) if the coverage area of the mapping procedure is identified as the target site for the ablation. Accordingly, each electrode 220 may also be configured to transmit energy to the corresponding region within the cardiac wall 20 during an ablation procedure.

The electrodes 220 may be configured such that one or more of the electrodes are independently operable to transmit energy to perform the ablation (e.g., independently of other electrodes of the medical device 200). In other words, if the mapping procedure identifies an area proximate the distal-most electrode 220 as the target site, and the areas corresponding to the locations of the other two electrodes appear to be normal, the distal-most electrode may be used to transmit energy for ablation, while the other electrodes remain inactive.

Although the above description provides some examples in which mapping is performed, followed by ablation, in some cases ablation may not be performed at all, or a second mapping procedure may be conducted following an ablation procedure to determine whether the ablation procedure was successful in minimizing or eliminating the cardiac arrhythmia.

The medical device 200 may be moved via the epicardial space 36 to a target site and inserted into the cardiac wall, as described above, by a surgeon using a tool that is separate from the medical device 200 to grip and manipulate the handle member 230 of the device 200. The tool for positioning the medical device 200 may, for example be inserted into the epicardial space via the second incision, described above, or via a third incision positioned proximate the first and/or second incisions.

In still other embodiments, a medical device 300 may be provided that is configured to be inserted through the cardiac wall with the electrodes initially in a retracted position and subsequently moved to an extended position such that the electrodes may engage a surface of the epicardium 34, such as an interface between the epicardium and the myocardium 40, or an inner surface of the endocardium 50, thereby effecting mapping and/or ablation of the endocardium via an epicardial approach.

Turning to FIGS. 9-11, for example, the medical device 300 may include a support member 310 defining a distal tip 312 that is configured to penetrate a thickness of the cardiac wall 20. The distal tip 312 may, for example, be tapered/bezeled and/or form a sharp point for puncturing the cardiac wall 20, in the manner of a syringe, as described above with respect to other embodiments. In this regard, in some embodiments, the support member 310 may have a diameter ranging from approximately 0.25 mm to approximately 2.5 mm, such as a diameter of approximately 2 mm. The medical device 300 may also include at least one mapping electrode 320 configured to move between a retracted position (shown in FIG. 9), in which the mapping electrode is disposed within a lumen of the support member 310, and an extended position (shown in FIG. 10), in which the mapping electrode is configured to engage a surface within the cardiac wall 20. In FIG. 10, for example, the mapping electrode 320 is positioned so as to engage the inner surface of the endocardium 50. Each electrode 320 may be configured to receive electrical impulses from a corresponding region within the cardiac wall. Thus, in FIG. 10, the mapping electrode 320 is positioned to receive electrical impulses from the surface with which the electrode is engaged.

Accordingly, in some embodiments, the mapping electrode 320 may be made of or coated with a shape memory alloy, such as nitinol, which is configured to return to a predefined shape when unconstrained in the extended position shown in FIG. 10. In the depicted embodiment, the mapping electrode 320 may define an engaging end 322 that is shaped to contact a surface within the cardiac wall. Thus, in some embodiments, when the mapping electrode 320 is in the retracted position shown in FIG. 9, the electrode may have a substantially linear shape as it is constrained by the inner wall of the support member 310. Once the distal tip 312 is positioned at the target site, e.g., by inserting the support member 310 into the layers of the cardiac wall 20, the support member may be moved proximally with respect to the mapping electrode 320 so as to unsheathe the mapping electrode, as shown in FIG. 10. In the unsheathed, extended position, the mapping electrode 320, by virtue of its shape memory properties, may achieve its predefined shape and may engage a corresponding surface of the cardiac wall 20.

In some cases, the mapping electrode 320 may be rotated once engaged with the appropriate surface within the cardiac wall 20. For example, the mapping electrode 320 may be selectively fixed to the support member 310 once in position, and the support member may be rotated, thereby also rotating the mapping electrode to map a circular coverage area. In other cases, the mapping electrode 320 may be independently rotatable with respect to the support member 310.

In some embodiments, the mapping electrode 320 may also be configured to transmit energy to a target site proximate the mapping electrode, e.g., to perform an ablation procedure using the same electrode. In other embodiments, however, the medical device 300 may further include a plurality of ablating electrodes 330 in addition to the mapping electrode 320. In the depicted embodiment, for example, four ablating electrodes 330 are provided, although in other embodiments the number of ablating electrodes may vary between 2 and 6 ablating electrodes or more (e.g., 12 ablating electrodes in some cases).

As described above with respect to other embodiments of the medical device, each ablating electrode 330 may be configured to transmit energy to a target site proximate a distal end 332 of the ablating electrode (FIG. 11). Each ablating electrode 330 may be configured to be received within the lumen of the support member when the ablating electrodes are in a retracted position, as shown in FIGS. 9 and 10. Each ablating electrode may further define a distal hook portion 332, shown in FIG. 11, when the ablating electrodes are in an extended position (e.g., are no longer confined within the support member). In this regard, the ablating electrodes 330 may be made of or coated with a shape memory alloy such as nitinol, such that when constrained by the support member 310 as depicted in FIG. 9, the ablating electrodes are relatively linear and are received within the support member. As the support member 310 is moved proximally with respect to the ablating electrodes 330, as shown in FIG. 11, the ablating electrodes may assume a predefined shape, which, in the depicted embodiment, includes a distal hook portion 332. Thus, in some embodiments, the hook portion 332 of each ablating electrode 330 may be configured to extend away from the support member 310 such that the distal hook portion of each ablating electrode engages a target site within the cardiac wall 20, such as a surface within the cardiac wall.

In some cases, the ablating electrodes 330 may be selectively fixed to the support member 310 once engaged with the appropriate surface within the cardiac wall 20 in the extended position, and the support member may be rotated, thereby moving the ablating electrodes in a circular path to ablate a circular coverage area.

In some embodiments, the medical device 300 may be used for performing a pacing procedure at local site within the cardiac wall 20 (e.g., in any of the three layers). For example, one or more of the ablating electrodes 330 or the mapping electrode 320 may be configured to transmit an electrical impulse for a predetermined period of time at a predetermined voltage during a pacing procedure. This may be done as a temporary measure, such as to stimulate the heart with electrical activity if necessary during a mapping or ablating procedure. In other cases, the medical device (e.g., the medical device 300) may be configured to deliver a permanent pacemaker to a location within the cardiac wall. For example, one or more of the electrodes 320, 330 (or a portion thereof) may be releasable from the support member 310 and may be configured to receive wireless energy transmissions from a location outside the patient's body so as to function as a permanent pacing device.

In still other embodiments, shown in FIGS. 12 and 13, a medical device 400 may be provided that, like the medical device 300, is configured to penetrate the layers of the cardiac wall to perform mapping and ablating procedures at locations within the cardiac wall. The medical device 400 may include a first support member 410 that defines a distal tip 412 configured to penetrate a thickness of the cardiac wall. A plurality of mapping electrodes 420 may be disposed along the first support member 410, and each electrode may be configured to receive the electrical impulses from a corresponding region within the cardiac wall 20. The first support member 410 and the mapping electrodes 420 may, for example, be configured as described above with respect to the medical device 100 and as illustrated in FIG. 2A.

The device 400 may further include a tubular member 450 that defines a lumen therethrough. The tubular member 450 may be configured to receive the first support member 410 within the lumen when the first support member is in a retracted position (not shown). In other words, the first support member 410 may be axially movable with respect to the tubular member 450. In an extended position, the distal tip 412 of the first support member 410 may be disposed distally of a distal end of the tubular member, as shown in FIGS. 12 and 13, such that the distal tip can penetrate the cardiac wall 20 for performing a mapping procedure of the layers 34, 40, 50 within the cardiac wall via the mapping electrodes 420.

In some embodiments, a transverse member 460 may be disposed on the distal end of the tubular member 450 and may be arranged substantially perpendicularly to the tubular member. The transverse member 460 may have a transverse dimension (e.g., a width or diameter) of approximately 0.5 cm to 4 cm, such as 1 cm to 2 cm, and may, in some cases, be collapsible, such that the transverse member may be delivered via a delivery sheath. In some cases, for example, the transverse member 460 may have a disk shape and/or may be integral to the tubular member 450. A plurality of second support members 411 may be provided that are supported by the transverse member 460, as shown. Each second support member 411 may define a distal tip 413 that is configured to penetrate a thickness of the cardiac wall 20. Each second support member 411 may be fixed to the transverse member 460, such that movement of the transverse member from the position shown in FIG. 12 to the position shown in FIG. 13 effects movement of the second support members for engaging and penetrating the different layers of the cardiac wall.

A plurality of ablating electrodes 430 may also be provided, with at least one ablating electrode disposed along each second support member 411. Each ablating electrode 430 may be configured to transmit energy to a target site proximate the ablating electrode, as described above with respect to other embodiments of the medical device 100, 200, 300.

As shown in FIG. 12, a mapping procedure may be performed through the layers of the cardiac wall 20 by moving the first support member 410 distally with respect to the tubular member 450, such that the distal tip 412 penetrates one or more of the layers, as shown in FIG. 12. The mapping electrodes 420 may then be used to map the electrical impulses through the thickness of the cardiac wall, as described above, for example, with respect to the medical device 200.

Based on the results of the mapping procedure, if ablation is required, the transverse member 460 carrying the second support members 411 may be moved distally, such as via distal movement of the tubular member 450 to which the transverse member is attached, such that each of the distal tips 413 of the second support members engage and penetrate one or more of the layers of the cardiac wall 20 (as shown in FIG. 13). Once the second support members 411 are in position, one or more of the ablating electrodes 430 on one or more of the second support members may be activated to ablate a corresponding area of the tissue within the cardiac wall, as necessary. For example, if ablation is required only in the myocardium 40, one or more of the ablating electrodes 430 corresponding to the areas in the myocardium requiring ablation may be activated independently of other ablating electrodes carried by the same second support member 411 (e.g., while the other ablating electrodes remain inactive). By selectively activating certain ablating electrodes 430 for the ablation procedure, an appropriate location (e.g., at the correct depth of the cardiac wall 20) and an appropriate coverage area (e.g., the correct amount of tissue) can be ablated. For example, by energizing a particular electrode 430 to a certain predetermined energy level for a predetermined amount of time, a certain radius of ablation may be achieved. Accordingly, by energizing the third electrode from the distal tip 412 on each of the second support members 411 (as an example), a combined coverage area may be achieved corresponding to the ablation of an appropriate radius and thickness of tissue.

In certain embodiments in which the medical device is configured to pierce through at least a portion of the cardiac wall, such as for the medical device 200, 300, 400 described above, bleeding may occur, which may obscure the user's view of the target area (e.g., in embodiments in which a fiber optic camera is used to position and monitor the distal end of the medical device) or may, in certain cases, otherwise adversely impact the mapping, ablating, and/or pacing procedure described above. Accordingly, embodiments of the invention may further provide for a containment device 500, shown in FIG. 14, that is configured to engage a portion of the epicardial surface via the pericardial space, fitting over the medical device 200, 300, 400, to contain any bleeding that may occur and, in some cases, remove excess blood from the vicinity via a suction port.

In this regard, embodiments of the containment device 500 may include a containment dome 510 configured (e.g., sized and shaped) to fit over a particular medical device. In the depicted embodiment of FIG. 14, for example, the containment dome 510 is configured to surround the tubular member 450 via a dome opening 515 and to fit over the transverse member 460. An engagement edge 520 of the containment dome 510 may be configured to contact the epicardial surface 35, such that any bleeding that results from the penetration of the layers of the cardiac wall 34, 40, 50 by the first and/or second support members 410, 411, in the depicted embodiment, may remain within the dome rather than spreading to other areas within the pericardial space. A suction port 540 may further be provided to withdraw at least a portion of the blood and other fluid from within the containment dome 510 by applying a light vacuum (e.g., between approximately 100 mmHg and 400 mmHg) to the interior of the containment dome. In this way, the user (e.g., the surgeon) may have a clearer view of the target site through the containment dome 510, which may be made of a transparent plastic material. In addition, providing a vacuum to the epicardial surface 35 at the target site may serve to counteract or at least dampen the movement of the cardiac wall 20 caused by each heartbeat, thereby providing for a more stable environment in which to conduct a mapping, ablating, or pacing procedure as described above.

In some cases, the containment dome 510 may be made of a collapsible material, such as a plastic material, that has an inherent resiliency such that the material may be collapsed to fit within a delivery device for delivery to the target site but, once released from the delivery device, can expand to assume a predetermined shape, such as the shape of the containment dome shown in FIG. 14. In this way, the containment device 500 may be delivered in a collapsed configuration to the location on the epicardial surface 35 where the mapping and ablation (for example) are to take place via a tubular delivery device, such as an outer sheath. The outer sheath may be disposed, for example, around the tubular member 450 of the embodiment of the medical device 400 shown in FIGS. 12 and 13, such that both the tubular member and the containment device 500 are delivered via the same tubular device (not shown). Once at the target site, the containment device 500 may be pushed out of the tubular device (or the tubular device may be retracted proximally with respect to the containment device) to release the containment device, thereby allowing the containment device to self-expand to its predefined shape (e.g., a dome shape) before engaging the epicardial surface 35.

In some embodiments, the containment device 500 may be configured such that a size and shape of the containment device 500 substantially corresponds to and/or accommodates the shape of the medical device. For example, depending on the type of medical device used and the particular configuration (e.g., size and shape) of the medical device, the containment device 500 may be configured to have a flatter profile, such that the distance between the dome opening 515 and the outer surface of the epicardium 34 is closer as compared to other embodiments where the distance needs to be greater to accommodate a longer medical device, for example.

With reference now to FIG. 17, another embodiment of a medical device for treating cardiac arrhythmias is shown. In FIG. 17, the medical device 700 comprises a plurality of support members 710, 711 that are configured to be moved between an expanded position (shown in FIG. 17) and a collapsed position, described in greater detail below. At least one mapping electrode 720 may be disposed on at least one of the support members 710, and the mapping electrode may be configured to receive electrical impulses such that the electrophysiology of the region of the heart proximate the mapping electrodes may be recorded and analyzed to identify abnormalities associated with the cardiac arrhythmia.

In the depicted embodiment, the medical device 700 includes a main support member 711 and four secondary support members 710 that extend outwardly from the main support member. Although four secondary support members 710 are shown, the medical device 700 may include any number of secondary support members, such as one, two, three, four, or more than four secondary support members, depending on the size, shape, curvature, and other properties of the target area to be addressed, the size of the medical device, and other considerations.

Each secondary support member 710 may comprise a support pad 715 that defines a containment dome 730. The containment dome 730, in turn, may be configured to apply a vacuum to a corresponding area of the epicardium for holding the respective support pad 715 (and, as a result, the medical device 700 itself) to the epicardial surface of the heart. Said differently, by applying a suction force via the containment dome 730 of each support pad 715, each support pad may be able to maintain a fixed position with respect to the epicardial surface for more accurately and efficiently carrying out mapping, ablating, and pacing procedures using the medical device, despite movement of the epicardial surface (e.g., due to the beating of the heart). In some embodiments, a vacuum pressure of approximately 50 mmHg to approximately 400 mmHg may be applied via the containment domes 730 to secure the medical device 700 to the epicardium.

Moreover, the secondary support members 710 may be independently movable about a connection point from which each secondary support member extends to enable the medical device to better conform to the shape of the epicardial surface (e.g., a surface that is not planar). With reference to FIG. 18, for example, in some embodiments, the medical device 700 may be configured such that in the expanded position a transverse axis T of the secondary support members 710 is at a slight angle θ with respect to a horizontal axis H extending through the main support member 711. In some embodiments, for example, the angle θ that is defined between the axis T and H is between 1° and 20°, such as 10°. The predefined angle θ of the medical device 700 in the expanded position may, in some cases, adjust (e.g., increase or decrease) as the medical device is placed at the target site and suction is applied via the containment domes 730, depending on the actual curvature of the surface of the epicardium in the area to which the medical device is applied.

In this regard, each secondary support member 710 (e.g., each support pad 715) may be attached to the main support member 711 via a connecting member 735, which may define a single connection point disposed between the main support member 711 and the respective secondary support member 710. The support pads 715 may thus be characterized, in some embodiments, as being able to "float" with respect to the main support member 711, thereby enabling the support pads to make better contact (and establish a better seal with) the epicardial surface.

In some embodiments, the containment domes 730 may be made of a flexible medical grade material that is configured to hold its shape under the vacuum pressures described above. The containment domes may also be self-sealing. For example, the containment domes may, in some embodiments, be made of a silicone material. In this regard, the containment dome 730 may be configured to receive a needle electrode therethrough (e.g., such as the medical device 200 described above with respect to the embodiments of FIGS. 7 and 8). The needle electrode may be configured to penetrate a thickness of the cardiac wall to perform mapping and/or ablation procedures within the cardiac tissue in regions of the heart corresponding to the locations of the containment domes 730. Thus, in some embodiments, the needle electrode may be configured to receive electrical impulses from a corresponding region within the cardiac wall during a mapping procedure and to transmit energy to the corresponding region within the cardiac wall during an ablation procedure, as described above.

In addition, each containment dome 730 may comprise a sealing ring 732, shown in FIGS. 20A and 20B, which may be configured to provide a seal and facilitate holding a vacuum pressure within the containment dome, as described above. The sealing ring 732 may, for example, be made of the same material as the containment dome 730, such as a silicone material, and in some cases may be integrally molded with the containment dome. In this regard, the sealing ring 732 may protrude past the planar contact surface of the support pad 715 (e.g., in the direction of the heart tissue) so as to provide a more effective seal against epicardial surface for the containment dome 730 for the vacuum.

Referring to FIGS. 17 and 19, each support pad 715 may comprise a peripheral edge 740 that extends outwardly from the containment dome 730 and defines a contact surface 745, at least part of which is configured to engage and form a seal with the epicardial surface. The electrodes 720 disposed on the secondary support members 710 (e.g., the mapping electrodes) may, in some cases, be disposed proximate a periphery of the respective support pad 715, such as on the peripheral edge 740. As shown in FIG. 19, which shows the contact surfaces 745 of the support pads 715, the electrodes 720 may protrude from the contact surfaces so as to engage the epicardial tissue and more accurately receive electrical impulses and/or transmit energy to the corresponding regions of the heart. In some embodiments, as shown in FIG. 20A, one or more of the electrodes 720 may be spring-loaded via holes 721 (shown also in FIG. 17) defined in the peripheral edge 740. In this way, the spring-loaded electrodes 720 may be biased towards engagement with the corresponding epicardial tissue and may more fully contact the tissue for carrying out mapping, ablating, and/or pacing procedures.

In some embodiments, the peripheral edge 740 of each support pad 715 may further include a peripheral sealing ring 734 in addition to or instead of the sealing ring 732 of the containment dome 730, as shown in FIG. 20B. The peripheral sealing ring 734 may be made of a hydrophobic or water repellant material (such as silicone) that is configured to provide a dry seal along the peripheral edge 740 of the support pad 715 to facilitate attachment of the respective support pad to the epicardial surface of the heart. In one embodiment, for example, a tacky silicone material may be used as the peripheral sealing ring 734 and may be applied to or integrally formed with the support pads 715.

Turning to FIGS. 17, 21, and 22, in some embodiments, the main support member 711 may define a first tubing portion 750 and a second tubing portion 755. The first tubing portion 750 may extend from a vacuum source (not shown) and may be in fluid communication with each containment dome 730. In this regard, the first tubing portion 750 may be in fluid communication with a lumen defined within the main support member 711, and the lumen may branch out from the main support member to each containment dome 730 via lumens defined within the connecting members 725. In some embodiments, for example, the connecting member 725 may comprise flexible tubing, such as tubing made of medical grade plastic material (e.g., a Tygon® coupler tube). Thus, in such embodiments, vacuum pressure from the vacuum source may be directed through the first tubing portion 750, through the lumen defined within the main support member 711, through a respective connecting member 725, and to the containment dome 730 for applying suction to the corresponding portion of the epicardial surface. The first tubing portion 750 may be made of a medical grade plastic material similar to the connecting members 725, such as Tygon® tubing.

With continued reference to FIGS. 17, 21, and 22, in some embodiments, the second tubing portion 755 may be configured to receive a guide member 760 therethrough. The guide member 760 may be movable by a user independently of the main support member 711 for positioning an electrode 722 disposed on the main support member with respect to the main support member, as described in greater detail below. For example, the guide member 760 may be slidable within the second tubing portion 755, such that a user may move the guide member along a longitudinal axis of the second tubing portion. Moreover, in some embodiments, a distal end of the guide member 760 may form or otherwise be attached to the electrode 722. Thus, in some embodiments, the guide member 760 may serve as both the conduit for transmitting energy from a power source outside the patient's body (e.g., during an ablation and/or pacing procedure) and/or receiving electrical impulses from the heart tissue (e.g., during a mapping procedure), as well as the vehicle for sliding the electrode along the main support member 711.

Referring to FIGS. 19 and 23, for example, a contact surface 746 of the main support member 711 may define a guide channel 765 along which the electrode 722 (which may be an ablating electrode) may be moveable. Thus, in some embodiments, the guide member 760 may comprise (at least in part) an electrically conductive material, such as 304 stainless steel. At least a proximal end of the guide member 760 may be coated with an electrically non-conductive material, e.g., plastic, or otherwise sheathed such that the proximal end of the guide member may be handled by the user to adjust the position of the electrode 722 along the channel 765. Furthermore, in some embodiments, one or more guide support wires 770 may be provided that extend from one end of the guide channel 765 to the other to support the electrode 722 as it is moved along the guide channel via movement of the guide member 760. For example, the electrode 722 may define a through hole (not shown), and a guide support wire 770 may be threaded through the through hole such that the electrode is slidable along the guide support wire. In other words, movement of the electrode 722 along the guide channel 765 may be stabilized and facilitated via the guide support wire 770. In this regard, the guide support wire 770 may be coated with a non-conductive material that also has a low coefficient of friction, such as Teflon® material, to avoid transmitting the energy provided for ablation procedures via the electrode 722 as well as to allow the electrode to easily slide from one end of the guide channel 765 to the other, as necessary.

In addition to the guide member 760, the second tubing portion 755 may also be configured to receive a cable harness 790 therethrough, where the cable harness allows energy to be transmitted to and/or from the electrodes 720 disposed on the secondary support member 710. For example, in the embodiment depicted in FIG. 17, in which four electrodes 720 are disposed on each of four secondary support members 710, the cable harness 790 may include sixteen contact wires for transmitting electrical impulses received from the heart tissue to equipment for mapping procedures and/or for providing energy from a power source to the electrodes for ablation and/or pacing procedures.

The first tubing portion 750 may, in some embodiments, be connected to the main support member 711 via a fitting, such as a barb fitting, for example. The second tubing portion 755 may, in some embodiments, be connected to the main support member via heat shrink, adhesive, or other types of mechanical or chemical connections.

The electrodes 720, 722 may be arranged in various ways on the support members 710, 711, depending on the particular configuration of the medical device 700, the support members 710, 711, and/or the support pads 715. For example, in the embodiment depicted in FIG. 19, each secondary support member 710 comprises a support pad 715 having a rounded rectangular shape when viewed from a contact surface side of the device 700. In the depicted embodiment, the containment dome 730 is disposed proximate the center of the support pad 715, and the electrodes 720 are distributed in the periphery around the containment dome in each of the four corners of the support pad. Although the depicted embodiment shows four electrodes 720 on each support pad 715, any number of electrodes may be provided on each support pad in various configurations, such as fewer than four electrodes or greater than four electrodes.

Accordingly, an overall shape of the distal end 701 of the medical device 700 is rectangular, as illustrated via the dashed lines in FIG. 19. In some embodiments, the distal end 701 of the medical device 700 may have an x-dimension ranging from approximately 4 cm to approximately 9 cm and y-dimension ranging from approximately 2 cm to approximately 7 cm, such as, for example, approximately 7 cm by approximately 5 cm. The dimensions of the distal end 701 may be selected to optimize the corresponding area of the heart tissue to be mapped and/or ablated, while at the same time ensuring that the device 700 will achieve appropriate levels of vacuum pressure to maintain the device in place during the procedure.

In other embodiments, the medical device 700 may have secondary support members 710 that are configured as shown in FIG. 24, where the support pads 715 have a rounded trapezoidal shape. In the embodiment of FIG. 24, the electrodes 720 may be arranged as shown, with one of the electrodes being in closer proximity to the containment dome 730 than the others due to the shape and available space provided by the peripheral edge 740. Accordingly, in the depicted embodiment of FIG. 24, the distal end 701 of the medical device 700 may have an oval shape, as shown by the dashed lines, and the x-y dimensions may be configured similarly to the x-y dimensions described with respect to the embodiment of FIG. 19.

Furthermore, as noted with respect to the embodiments described above, in some cases, an optical device, such as a fiber optic camera, may be advanced to the patient's pericardial space to allow the user to visually monitor the position of the medical device 700 with respect to the location of the heart to be mapped. The optical device may be configured to capture and transmit an epicardial view of the cardiac tissue (e.g., a view of the heart taken from the pericardial space). Using the epicardial view, the user may be able to position the medical device 700 proximate the desired location (e.g., the target site), and the electrical impulses received from the target site may be mapped via the mapping electrodes 720, 722 provided on the support members 710, 711. In this regard, in some embodiments, a grasping ring 780 (shown, e.g., in FIG. 17) may be provided on or as part of the main support member 711 to allow the user to hold and more accurately position the medical device 700 with respect to the epicardial surface of the patient's heart prior to and/or while applying suction to secure the medical device 700 in place with respect to the epicardium.

As noted above with respect to other embodiments, once an appropriate surface of the epicardium is mapped and analyzed, and the user has identified a target site for ablation, the medical device 700 may further be used to ablate epicardial tissue, such as via the electrode 722. In some cases, the electrodes 720 provided on the support pads 715 may also be configured for both ablating and mapping procedures, as well as for temporary pacing procedures. The operation of the electrodes 720, 722 may be the same as that described above with respect to embodiments of the invention related to FIGS. 2-5. Thus, as described above, the electrodes 720, 722 provided on the support members 710, 711 may allow electrophysiological data to be collected over a surface of epicardium 34 (FIG. 1A), with each electrode configured to receive electrical impulse data from a location on the epicardium corresponding to the location of the electrode. In addition or alternatively to being a mapping electrode, at least some of the electrodes 720, 722 may be configured as ablating electrodes that are configured to transmit energy to a target site proximate the ablating electrode during an ablation procedure. Furthermore, in some embodiments, the electrodes 720, 722 may be configured to transmit the electrical impulses for a predetermined period of time at a predetermined voltage proximate the target site so as to provide temporary pacing.

Turning now to FIG. 25, a method of treating cardiac arrhythmias using a medical device 700 as illustrated and described above with reference to FIGS. 17-24 is provided. According to embodiments of the method, an incision may be made in the thoracic area of the patient's body, which may be, for example, approximately 1 cm to approximately 2.5 cm long. FIG. 25, Block 800. The incision may provide a port for inserting and positioning the medical device 700, which, as described above, may include a main support member, at least one secondary support member extending outwardly from the main support member, and at least one electrode configured to receive electrical impulses disposed on each secondary support member. As described above, each secondary support member may comprise a support pad with a containment dome.

The medical device may be moved to a collapsed state by the surgeon prior to insertion through the port, such as by folding the device 700 along a folding axis F in the direction of the arrows f, as shown in FIG. 17. Block 810. The medical device may then be advanced in the collapsed position (e.g., being held in the folded configuration by the surgeon via a surgical instrument, such as forceps) to a target site on the epicardium of the heart at Block 820 and may be expanded proximate the target site at Block 830. Each support pad of the secondary support members may then be removably attached to a corresponding area of the epicardium for fixing the medical device with respect to the surface of the heart. Block 840.

In some embodiments, as described above, each support pad may define a containment dome. Accordingly, in some cases, a vacuum may be applied to the corresponding area of the epicardium via the containment domes for holding the respective support pad thereto. Moreover, in some embodiments, the medical device may further comprise at least one ablating electrode configured to transmit energy to a target site proximate the electrode that is slidably disposed along the main support member, as described above. In such cases, the ablating electrode may be moved with respect to the main support member so as to ablate portions of cardiac tissue via the ablating electrode.

Accordingly, embodiments of a medical device are described above for performing mapping, ablating, and/or pacing procedures on one or more layers of the cardiac wall via an epicardial approach in a minimally invasive (e.g., orthoscopic) surgical procedure. As described above, a surface of the heart may be mapped at the time of surgical revascularization after a large myocardial infarction to both diagnose and potentially treat life-threatening arrhythmias. Through an epicardial approach, coronary arteries located on the surface of the heart may be avoided, while at the same providing the user (e.g., the surgeon) with access to tissue in any of the layers of within the cardiac wall, as necessary, through embodiments of the medical device that penetrate through a thickness of the cardiac wall. In this way, cardiac arrhythmias may be identified, located, and addressed with minimal risk to the patient and in a way that is more accurate, safer, and more repeatable than conventional mapping and ablating procedures.

Embodiments of a method for treating cardiac arrhythmias may include making a first incision in a thoracic area of a patient's body, inserting a distal end of a medical device into the first incision, making a second incision in the thoracic area of the patient's body, inserting an optical device into the second incision, where the optical device is configured to capture and transmit an epicardial view of the target site, and positioning the distal end of the medical device proximate the target site using the epicardial view. As described above with reference to the figures, the medical device may be configured to be delivered to the target site epicardially and may include a plurality of mapping electrodes configured to receive electrical impulses and at least one ablating electrode configured to transmit energy to a target site proximate the ablating electrode. The electrical impulses received from the target site may be mapped using the medical device, and portions of cardiac tissue may be ablated using the medical device based on the electrical impulses received. Furthermore, in some embodiments, the patient's heart function may be paced using the medical device by transmitting an electrical impulse for a predetermined period of time at a predetermined voltage proximate the target site, as described above.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A medical device for treating cardiac arrhythmias comprising:
    a main support member;
    a plurality of secondary support members, wherein the secondary support members are radially movable relative to a longitudinal axis of the main support member between an expanded position and a collapsed position;
    a plurality of mapping electrodes, at least one mapping electrode being disposed on each secondary support member, each mapping electrode being configured to receive electrical impulses; and
    an ablating electrode slidably disposed on the main support member, wherein a contact surface of the main support member defines a guide channel along which the ablating electrode is movable, wherein the ablating electrode is axially movable relative to the longitudinal axis of the main support member, the ablating electrode being configured to transmit energy to a target site proximate the ablating electrode, wherein, in the expanded position, the secondary support members define a coverage area and the mapping electrodes are configured to receive electrical impulses from corresponding locations of the target site across the coverage area, and wherein, in the expanded position, the ablating electrode is axially movable along the main support member to ablate a portion of the target site within the coverage area.

2. The medical device of claim 1 further comprising a guide member attached to the ablating electrode, wherein the guide member is movable by a user independently of the secondary support members for positioning the ablating electrode.

3. The medical device of claim 1 further comprising a tubular member defining a lumen therethrough, wherein the tubular member is configured to receive the secondary support members within the lumen when the secondary support members are in the collapsed position.

4. The medical device of claim 1, wherein the secondary support members extend outwardly from the main support member.

5. The medical device of claim 4, wherein the secondary support members are independently movable about a connection point from which each secondary support member extends, each connection point being disposed between the main support member and the respective secondary support member.

6. The medical device of claim 4, wherein each secondary support member comprises a support pad, wherein each support pad defines a containment dome configured to apply a vacuum to a corresponding area of an epicardium for holding the respective support pad thereto.

7. The medical device of claim 6, wherein the mapping electrodes are disposed proximate a periphery of the respective support pad.

8. The medical device of claim 6, wherein each containment dome receives a needle electrode therethrough, wherein the needle electrode is configured to penetrate a thickness of a cardiac wall.

9. The medical device of claim 8, wherein each needle electrode is configured to receive electrical impulses from a corresponding region within the cardiac wall during a mapping procedure and to transmit energy to the corresponding region within the cardiac wall during an ablation procedure.

10. The medical device of claim 6, wherein the main support member defines a first tubing portion and a second tubing portion, wherein the first tubing portion extends from a vacuum source and is in fluid communication with each containment dome, and wherein the second tubing portion is configured to receive a guide member therethrough, the guide member being movable by a user independently of the main support member for positioning the ablating electrode with respect to the main support member.

11. The medical device of claim 1, wherein at least some of the mapping electrodes are configured to transmit energy independently of other mapping electrodes during an ablation procedure.

12. The medical device of claim 1, wherein the main support member is a central support member that is centrally disposed with respect to the plurality of secondary support members.

13. A medical device for treating cardiac arrhythmias comprising:
    a main support member;
    a plurality of secondary support members extending outwardly from the main support member, wherein the secondary support members are radially movable relative to a longitudinal axis of the main support member between an expanded position and a collapsed position; and
    a plurality of mapping electrodes, at least one mapping electrode being disposed on each of the secondary support members, the mapping electrodes being configured to receive electrical impulses, wherein the secondary support members each comprise a support pad configured to be removably attached to a corresponding area of an epicardium for holding the medical device in place during a procedure, and wherein each support pad defines a containment dome configured to apply a vacuum to the corresponding area of the epicardium for holding the respective support pad thereto.

14. The medical device of claim 13 further comprising at least one ablating electrode configured to transmit energy to a target site proximate the mapping electrodes, wherein the at least one ablating electrode is slidably disposed on the main support member such that the ablating electrode is axially movable relative to the longitudinal axis of the main support member.

15. The medical device of claim 13, wherein the medical device is collapsible about the main support member for delivery to a target site.

16. A medical device for treating cardiac arrhythmias, the device comprising:
    a main support member;
    a plurality of secondary support members wherein the secondary support members extending outwardly from the main support member, each secondary support member comprising a support pad, and each support pad defining a containment dome configured to apply a vacuum to a corresponding area of an epicardium for holding the respective support pad thereto, wherein the secondary support members are radially movable relative to a longitudinal axis of the main support member between an expanded position and a collapsed position;
    a plurality of mapping electrodes, at least one mapping electrode being disposed on each secondary support member, each mapping electrode being configured to receive electrical impulses; and
    an ablating electrode slidably disposed on the main support member, wherein the ablating electrode is axially movable relative to the longitudinal axis of the main support member, the ablating electrode being configured to transmit energy to a target site proximate the ablating electrode, wherein, in the expanded position, the secondary support members define a coverage area and the mapping electrodes are configured to receive electrical impulses from corresponding locations of the target site across the coverage area, and wherein, in the expanded position, the ablating electrode is axially movable along the main support member to ablate a portion of the target site within the coverage area.

17. The medical device of claim 16, wherein the mapping electrodes are disposed proximate a periphery of the respective support pad.

18. The medical device of claim 16, wherein each containment dome receives a needle electrode therethrough, wherein the needle electrode is configured to penetrate a thickness of a cardiac wall.

19. The medical device of claim 18, wherein each needle electrode is configured to receive electrical impulses from a corresponding region within the cardiac wall during a mapping procedure and to transmit energy to the corresponding region within the cardiac wall during an ablation procedure.

20. The medical device of claim 16, wherein the main support member defines a first tubing portion and a second tubing portion, wherein the first tubing portion extends from a vacuum source and is in fluid communication with each containment dome, and wherein the second tubing portion is configured to receive a guide member therethrough, the guide member being movable by a user independently of the main support member for positioning the ablating electrode with respect to the main support member.

21. A method of treating cardiac arrhythmias comprising:
    making an incision in a thoracic area of a patient's body;
    providing a medical device in a collapsed position for insertion through the incision, wherein the medical device comprises:
        a main support member;
        a plurality of secondary support members extending outwardly from the main support member, wherein the secondary support members are radially movable relative to a longitudinal axis of the main support member between an expanded position and a collapsed position, and wherein the secondary support members each comprise a support pad configured to be removably attached to a corresponding area of an epicardium for holding the medical device in place during a procedure, each support pad defining a containment dome configured to apply a vacuum to the corresponding area of the epicardium for holding the respective support pad thereto; and a plurality of mapping electrodes, at least one mapping electrode being disposed on each of the secondary support members;

advancing the medical device to a target site on the epicardium;

radially moving the secondary support members relative to the main support member proximate the target site; and removably attaching the support pads of the secondary support members to a corresponding area of the epicardium.

22. The method of claim 21, further comprising applying a vacuum to the corresponding area of the epicardium for holding the respective support pad thereto.

23. The method of claim 21, wherein the medical device further comprises at least one ablating electrode configured to transmit energy to the target site, the at least one ablating electrode being slidably disposed over the main support member, the method further comprising moving the ablating electrode with respect to the longitudinal axis of the main support member and ablating portions of cardiac tissue via the ablating electrode.

\* \* \* \* \*